US006262094B1

(12) United States Patent
Hoefle et al.

(10) Patent No.: US 6,262,094 B1
(45) Date of Patent: *Jul. 17, 2001

(54) C-21 MODIFIED EPOTHILONES

(75) Inventors: Gerhard Hoefle; Nicole Glaser, both of Braunschweig; Thomas Leibold, Wolfenbuttel, all of (DE); Gregory Vite, Titusville; Soong-Hoon Kim, Lawrenceville, both of NJ (US)

(73) Assignee: Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/506,481

(22) Filed: Feb. 17, 2000

(30) Foreign Application Priority Data

Feb. 22, 1999 (DE) ............................................... 199 07 588
Jul. 1, 1999 (DE) ............................................... 199 30 111

(51) Int. Cl.$^7$ ....................... C07D 417/06; A61K 31/425

(52) U.S. Cl. ........................................... 514/365; 548/204

(58) Field of Search ............................ 548/204; 514/365

(56) References Cited

FOREIGN PATENT DOCUMENTS

| | | |
|---|---|---|
| 41 38 042 A1 | 5/1993 | (DE) . |
| 195 42 986.9 | 11/1995 | (DE) . |
| 196 39 456.2 | 9/1996 | (DE) . |
| 196 47 580.5 | 11/1996 | (DE) . |
| 196 36 343.8 | 2/1997 | (DE) . |
| 196 45 361.5 | 2/1997 | (DE) . |
| 196 45 362.3 | 2/1997 | (DE) . |
| 197 07 303.3 | 2/1997 | (DE) . |
| 197 01 758 A1 | 7/1998 | (DE) . |
| 197 13 970 A1 | 10/1998 | (DE) . |
| 197 20 312 A1 | 11/1998 | (DE) . |
| 198 21 954 A1 | 11/1998 | (DE) . |
| 197 26 627 A1 | 12/1998 | (DE) . |
| 0 879 605 A2 | 11/1998 | (EP) . |
| WO 93/10121 | 5/1993 | (WO) . |
| WO 97/19086 | 5/1997 | (WO) . |
| WO 99/03848 | 7/1997 | (WO) . |
| WO 98/22461 | 11/1997 | (WO) . |
| WO 98/08849 | 3/1998 | (WO) . |
| WO 9822461 | 5/1998 | (WO) . |
| WO 98/24427 | 6/1998 | (WO) . |
| 98/25929 * | 6/1998 | (WO) ................................... 548/204 |
| WO 98/38192 | 9/1998 | (WO) . |
| WO 98/47891 | 10/1998 | (WO) . |
| WO 99/01124 | 1/1999 | (WO) . |
| WO 99/03848 | 1/1999 | (WO) . |
| WO 99/07692 | 2/1999 | (WO) . |
| WO 9954330 | 10/1999 | (WO) . |
| WO 9967252 | 12/1999 | (WO) . |

OTHER PUBLICATIONS

International Search Report issued by European Patent Office for corresponding international application date Jun. 14, 2000 (date of mailing Jul 4,2000).

M. Seffow, et al., "Substitution at the Thiazole Moiety of Epothline" Heterocycles, col. 48, No. 12, 1998, pp. 2485–2488.

G. Hofle, et al., "N–Oxidation of Epothiline A–C and O–Acyl Rearrangement of C–19– and C–21–Substituted Epothilones" Angewandte Chemie, International Edition, vol. 38, No. 13/14, 1999, pp. 1971–1974.

K.C. Nicolaou et al., "Total Synthesis of Epothilone E and Related Side Chain Modified Analogues via a Stille Coupling Based Strategy" Bioorganic And Medical Chemistry, vol. 7, No. 5, 1999, pp. 665–697.

Hofle, "N–Oxidation of Epothiconbe A–C and O–Acyl...", Agnew. Chem. Int. Ed. 1999, 38, No. 13/14, pp. 1971–1974.

Inokuchi, "Opening of Epoxides to Olefino or Halohydrino with Vandaium...", Synlett, Jun. 1992, pp. 510–512.

Kowalski, "Activities of the Microtubule–Stabilizing Agents...", The Journal of Biological Chemistry, vol. 272, No. 4, issue of Jan. 24, pp.2534–2541.

Kupchan, "Reductive Elimination of Epoxides to Olefins with Zinc–Copper Couple", J. Org. Chem., vol. 36, No. 9, 1971, pp. 1187–1190.

Martin, "Epoxides as Alkene Protecting Groups. A Mild and Efficient Deoxygenation", Tetrahedron Letters, vol. 25, No. 3, 1984, pp. 251–254.

McMurry, "Reduction of Epoxides to Olefins with Low Valent Titanium", J. Org. Chem., vol. 40, No. 17, 1975, pp. 2555–2556.

McMurry, "Some Deoxygenation Reactions with Low–Valent Titanium", The Journal of Organic Chemistry, vol. 43, No. 17, August 18, 1978, pp. 3249–3254.

Meng, "Remote Effects in Macrolide Formation through Ring–Forming...", Communications to the Editor, 1997.

Nicolaou, "An Approach to Epothilones based on Olefin Metathesis", Agnew. Chem. Int. Ed. Engl. 1996, 35, No. 20, pp. 2399–2401.

Nicolaou, "Total Synthesis of Epothilone A: The Macrolactonization Approach", Agnew. Chem. Int. Ed. Engl. 1997, 36, No. 5, pp. 525–527.

Nicolaou, "Designed Epothilones: Combinatorial Synthesis, Tublin Assembly Properties...", Agnew.Chem.Int.Ed. Engl. 1997, 36, No. 19, pp. 2097–2103.

(List continued on next page.)

Primary Examiner—Robert Gerstl
(74) Attorney, Agent, or Firm—Rena Patel

(57) ABSTRACT

The invention is concerned with epothilones in which the thiazole substituent has been modified, with methods for their preparation and with antifungal or therapeutic agents which contain these epothilones.

29 Claims, No Drawings

OTHER PUBLICATIONS

Nicolaou, "The Olefin Metathesis Approach to Epothilone A and its Analogues", J.Am. Chem. Soc. 1997, 119, pp. 7960–7973.

Nicolaou, "Total Syntheses of Epothilones A and B...", J.Am. Chem. Soc. 1997, 119, pp.7974–7991.

Nicolaou, "Syntheses of Epothilones A and B...", Nature, vol. 387, 15 May 1997, p. 268–272.

Correction: Nicolaou, "Synthesis of epothilones A and B in solid and solution phase", Nature 387, pp. 268–272 (1997).

Raucher, "Total Synthesis of (+) –Dihydrocostunolide via Tandem Cope–Claisen Rearrangement", J. Org. Chem. 1986, 51 pp. 5503–5505.

Sato, "Reduction of Organic Compounds with Low–Valent Niobium", Chemistry Letters, 1982, pp. 157–160.

Schnizer, "Total Synthesis of (–) –Epothilone A", Agnew. Chem. Int. Ed. Engl. 1997, 36, No. 5, pp. 523–525.

Schobert, "Reduction and Isomerization of Oxiranes and a–Diazoketones by Various Early Transition Metallocenes", Synlett, 1990, No. 8, Aug., pp. 465–466.

Sharpless, "Lower Valent Tungsten Halides. A New Class of Reagents for Deoxygenation of Organic Molecules", Journal of American Chemical Society, 94:18, Sep. 6, 1972, pp. 6538–6540.

Su, "Total Synthesis of (–) –Epothilone B: An Extension of the Suzuki Coupling Method and Insights into Structure–Activity Relationships of the Epothilones", Angew. Chem. Int. Ed. Engl. 1997, 36, No. 7, pp. 737–759.

Su, "Structure–Activity Relationships of the Epothilones and the First In Vivo Comparison with Paclitaxel", Angew. Chem. Int. Ed. Engl. 1997, 36, No. 19, pp. 2093–2096.

Victory, "Relative Stereochemistry and solution conformation of the novel paclitaxel–like antimitotic agent epothilone A", Biorganic & Medicinal Chemistry Letters, vol. 6, No. 7, pp. 893–898.

Winkler, "A Model For the taxol (Paclitaxel)/Epothilone Pharmacophore", Biorganic & Medicinal Chemistry Letters, vol. 6, No. 24, pp. 2963–2966.

Bollag, "Epothilones, a new structural class of microtubule stabilizer", Experimental Therapeutics, Proceedings of the American Association for Cancer Research, vol. 36, Mar. 1995, p. 454.

Bollag, "Review, Oncologic, Endocrine & Metabolic, Epothilones: novel microtubule–stabilising agents", Exp. Opin. Invest. Drugs (1997) 6(7), pp. 867–873.

Bertinato, "Studies toward a Synthesis of Epothilone A: Stereocontrolled Assembly of the Acyl Region and Models for Macrocyclization", J. Org. Chem. 1996, 61, pp. 8000–8001.

Borman, "Epothilone Epiphany: Total Syntheses", Chem & Eng News, Dec. 23, 1996, vol. 74, No. 52, pp. 24–26.

"First total synthesis of epothilone B", Chem & Eng News, Mar. 31, 1997, vol. 75, No. 13, p. 23.

"Solid–phase epothilone synthesis used to create analog library", Chem & Eng News, May 19, 1997, vol. 75, no. 20, p. 33.

Claus, "Synthesis of the C1–C9 Segment of Epothilons", Tetrahedron Letters, vol. 38, No. 8, pp. 1359–1362.

De Brabander, "Towards a Synthesis of Epothilone A: Rapid Assembly of the C1–C6 and C7–C12 Fragments", Synlett, Jul. 1997, pp. 824–826.

Gabriel, "The Chromium–Reformatsky Reaction: Asymmetric Synthesis of the Aldol Fragment of the Cytotoxic Epothilons from 3–(2–Bromoacyl)–2–oxazolidinones", Tetrahedron Letters, vol. 38, No. 8, pp. 1363–1366.

Gerth, "Epothilons A and B: Antifungal and Cytotoxic Compounds from Sorangium cellulosum (Myxobacteria) Production, Physico–chemical and Biological Properties", The Journal of Antibiotics, Jun. 1996., pp. 560–563.

Marshall, "Total synthesis of epothilone", Nature Biotechnology, vol. 15, Mar. 1997, p. 205.

Meng, "Studies toward a Synthesis of Epothilone A: Use of Hydropyran Templates for the Management of Acyclic Stereochemical Relationships", J. Org. Chem. 1996, 61, pp. 7998–7999.

Meng, "Total Syntheses of Epothilones A and B", J. Am. Chem. Soc. vol. 119, No. 42, pp. 10073–10092.

Mensching, "Generation of Thiazoles by Column Dehydrogenation of Thiazolidines with MnO2", J. prakt. Chem. 339 (1997), pp. 96–97.

Mulzer, "Synthesis of C(1) –C(9) Segment of the Cytotoxic Macrolides Epohilon A and B", Tetrahedron Letters, vol. 37, No. 51 pp. 9179–9182.

Nicolaou, "Chemistry, Biology and Medicine of Selected Tubulin Polymerizing Agents", Pure Appl. Chem. vol. 71, No. 6, pp. 989–997.

Schinzer, "Studies Towards the Total Synthesis of Epothilones: Asymmetric Synthesis of the Key Fragments", Chem. Euro. J. 1996 2 No. 11, pp. 1477–1482.

Taylor, "Towards the Synthesis of Epothilone A: Enantioselective Preparation of the Thizole Sidechain and Macrocyclic Ring Closure", Tetrahedron Letters, vol. 38, No. 12, pp. 2061–2064.

Schinzer, "Total Synthesis of(–)Epothilone A", Chem. Eur. J. 1999, 5, No. 9, pp. 2483–2491.

Schinzer, "Syntheses of (–) Epothilone B", Chem. Eur. J. 1999, 5, No. 9, pp. 2492–2500.

Nicolaou, "Synthesis and Biological Properties of C12, 13–cyclopropyl–epothilone A and related epothilones", Chemistry and Biology 1998, vol. 5, No. 7, pp. 365–372.

Bertini, "Alkenes from Epoxides by Reductive Elimination with Magnesium Bromide–Magnesium Amalgam", Chemical Communications, 1970, p. 144.

Bollag, "Epothilones, a New Class of Microtubule–stabilizing Agents with a Taxol–like Mechanism of Action", Cancer Research 55, Jun. 1, 1995, pp. 2325–2333.

Fujisawa, "Deoxygenation of Epoxides to Olefins with FeCI3 –n –BuLi System", Chemistry Letters, 1974, pp. 883–886.

Fujiwara, "Reductive Coupling of Carbonyl Compounds to Olefins by Tungsten Hexachloride–Lithium Aluminum Hudride and Some Tungsten and Molybdenum Carbonyls", J. Org. Chem. vol. 43, No. 12, pp. 2477–2479.

Gladysz, "Deoxygenation of Epoxides by Metal Atom Concondensation", J. Org. Chem., vol. 41, No. 22, 1976, pp. 3647–3648.

Hofle, "Epothilone A and B–Novel 16–Membered Macrolides with Cytotoxic Activity: Isolation, Crystal Structure, and Conformation in Solution", Angew, Chem. Int. Ed. Engl. 1996, 35, No. 13 14, pp. 1567–1569.

"Total Synthesis of (–)–Epothilone A"Angew. Chem. Int. Ed. Engl. 1996, 35, No. 23.24, pp. 2801–2803.

Abstract of DE 19701758 A, "New beta–keto–alcohol derivatives –useful as intermediates for epothilone(s)", Jan. 20, 1997.

Abstract of DE 19713970, "Preparation of prenyl derivatives as building blocks for epothilones", Oct. 8, 1998.
Abstract of DE 1970705.3, Feb. 25, 1997.
Abstract of WO 98/38192, "Production of modified epothilone compounds –e.g. from epothilone A or B by hidrogenation, halogenation, epoxidation, N–oxidation, metallation and electrophilic substitution", Sept. 3, 1998.
Abstract of DE 1007505, Feb. 25, 1997.
Abstract of DE 19645361, Apr. 30, 1998.
Abstract of DE 19645362, 04/30/98.
Abstract of WO 98/08849, "Production of epothilone compounds with taxol–like activity –by total synthesis from new thiazolyl–hydroxy–alkyl–diene and protected dihydroxy–oxo–tridecenoic acid intermediates", Mar. 5, 1998.
Abstract of DE 19636343.
Abstract of WO 9310121, May 27, 1993.
Abstract of EP 879605, Nov. 25, 1998.
Abstract of DE 19726627, Dec. 24, 1998.
Abstract of WO 9719086, "Preparation of epothilone derivatives as agrochemicals and pharmaceuticals", May 29, 1997 and Abstract of DE 4138042, "Epothilone derivatives", May 27, 1993.
Miscellaneous Abstracts titled "Note–epothilones and Sloan–Kettering".
Miscellaneous Abstracts, pp. 51, 3, 4.
Miscellaneous Abstracts, pp. 37, 1–3.
Yang, "Total Synthesis of Epothilone A: The Olefin Metathesis Approach", Angew. Chem. Int. Ed. Engl. 1997, 36, No. 1,2, pp. 166–168.

* cited by examiner

C-21 MODIFIED EPOTHILONES

SUMMARY OF THE INVENTION

This invention concerns a compound having the general formula I

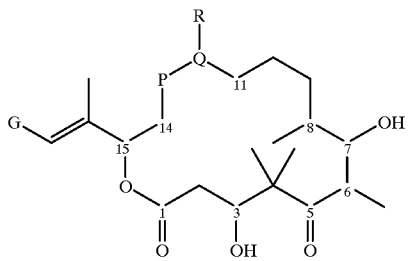

where:
P—Q is a C, C double bond or an epoxide;
G is N

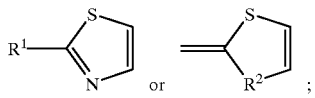

R is selected from the group of H, alkyl, and substituted alkyl;
$R^1$ is selected from the group consisting of

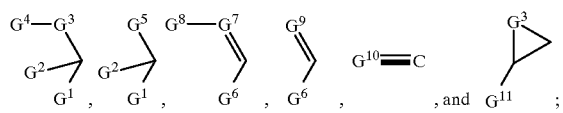

$R^2$ is

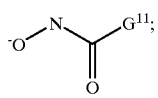

$G^1$ is selected from the group of H, halogen, CN, alkyl and substituted alkyl;
$G^2$ is selected from the group of H, alkyl, and substituted alkyl;
$G^3$ is selected from the group of O, S, and $NZ^1$;

This application claims priority from German applications DE 199 07 588.3, filed Feb. 22, 1999 and DE 199 30 111.5, filed Jul. 1, 1999, incorporated herein by reference in their entirety.

BACKGROUND OF THE INVENTION

Epothilones are macrocyclic lactones with useful antifungal and cytotoxic properties. Their action, as in the case of Taxol$^R$, is based on stabilization of the microtubuli as a result of which especially tumors and other rapidly dividing cells are inhibited. Typical epothilones carry a methylthiazolyl side chain, a 12,13-double bond (C, D), a 12,13-epoxide (A, B) and a proton (A, C) or a methyl group (B, D) on C-12; compare, for example: Review *Angew. Chem.* 1998, 110, 89–92 and 2120–2153 and *Heterocycles* 1998, 48, 2485–2488.

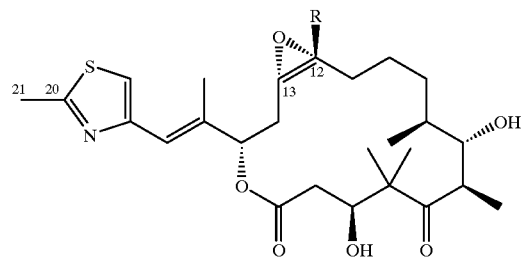

Epothilone A, R = H
B, R = Me

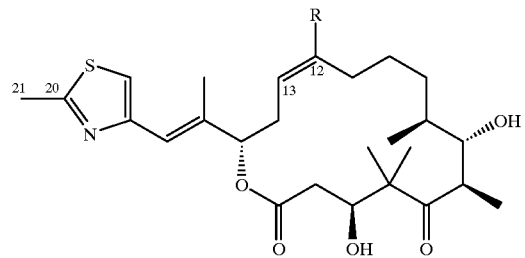

Epothilone C, R = H
D, R = Me $G^4$ is selected from the group of H, alkyl, substituted alkyl, $OZ^2$, $NZ^2Z^3$, $Z^2C$=O, $Z^4SO_2$, and optionally substituted glycosyl;

$G^5$ is selected from the group of halogen, $N_3$, NCS, SH, CN, NC, $N(Z^1)_3^+$, and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}OZ^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

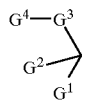

$G^1$, $G^2$, $G^3$ and $G^4$ cannot simultaneously have the following meanings:

$G^1$ and $G^2$=H, $G^3$=O and $G^4$=H or $Z^2C$=O where $Z^2$=alkyl group.

Further, the invention concerns a compound having general formula Ia

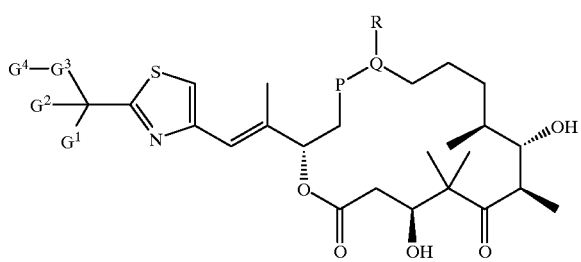

where the symbols have the following meaning:

P—Q is a C,C double bond or an epoxide,

R is a H atom or a methyl group, $G^1$ is a H atom, an alkyl group, a substituted alkyl group or a halogen atom, $G^2$ is a H atom, an alkyl group or a substituted alkyl group, $G^3$ is an O atom, an S atom or an $NZ^1$ group with $Z^1$ being a H atom, an alkyl group, a substituted alkyl group, an acyl group, or a substituted acyl group, and $G^4$ is a H atom, an alkyl group or a substituted alkyl group, an $OZ^2$ group, an $NZ^2Z^3$ group, a $Z^2C$=O group, a $Z^4$ $SO_2$ group or an optionally substituted glycosyl group with $Z^2$ being a H atom, an alkyl group, a substituted alkyl group, an aryl group, a substituted aryl group or a heterocyclic group, $Z^3$ a H atom, an alkyl group, a substituted alkyl group, an acyl group or a substituted acyl group, and $Z^4$ an alkyl group, a substituted alkyl group, an aryl group, a substituted aryl group or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C$=O with $Z^2$=alkyl group.

Further, the invention concerns a compound having general formula Ib

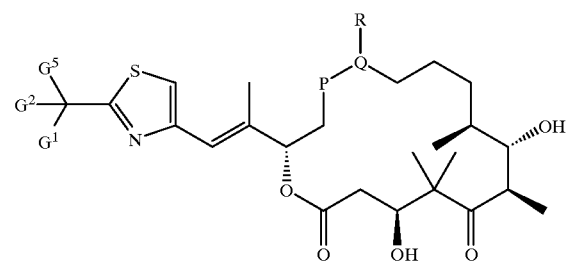

where the symbols have the following meaning:

P—Q is a C,C double bond or an epoxide,

R is a H atom or a methyl group, $G^1$ is a H atom, an alkyl group, a substituted alkyl group or a halogen atom, $G^2$ is a H atom, an alkyl group or a substituted alkyl group, and $G^5$ is a halogen atom, an $N_3$ group, an NCS group, an SH group, an CN group, an NC group or a heterocyclic group.

Further, the invention concerns a compound having general formula IIa

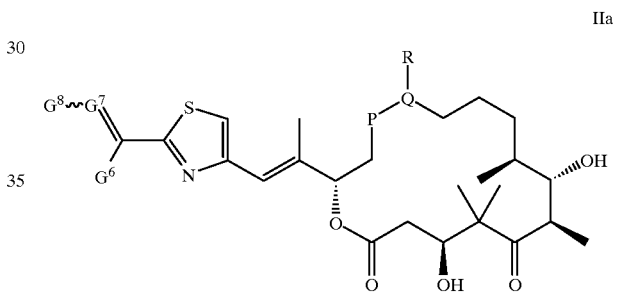

where the symbols have the following meaning:

P—Q is a C,C double bond or an epoxide,

R is a H atom or a methyl group, $G^6$ is a H atom, an alkyl group, a substituted alkyl group or a $CF_3$, $OZ^5$, $SZ^5$ or $NZ^5Z^6$ group with $Z^5$ being a H atom, an alkyl group, a substituted alkyl group, an acyl group or a substituted acyl group, and $Z^6$ being a H atom, an alkyl group or a substituted alkyl group, $G^7$ is a $CZ^7$ group or an N atom with $Z^7$ being a H or halogen atom, an alkyl group, a substituted alkyl group, an aryl group, or a substituted aryl group, or an $OZ^8$, $SZ^8$ or $NZ^8Z^9$ group with $Z^8$ being a H atom, an alkyl group, a substituted alkyl group, an acyl group or a substituted acyl group, and $Z^9$ being a H atom or an alkyl group, and $G^8$ is a H or a halogen atom, an alkyl group or an $OZ^{10}$, $SZ^{10}$ or $NZ^{10}Z^{11}$ group with $Z^{10}$ being a H atom, an alkyl group, a substituted alkyl group, an acyl group, a substituted acyl group, an aryl group, or a substituted aryl group, and $Z^{11}$ being a H atom, an alkyl group, a substituted alkyl group, an acyl group, or a substituted acyl group.

Further, the invention concerns a compound having general formula IIb where the symbols have the following meaning:

P—Q is a C,C double bond or an epoxide,

R is a H atom or a methyl group, $G^6$ is a H atom, an alkyl group, a substituted alkyl group or a $CF_3$, $OZ^5$, $SZ^5$ or $NZ^5Z^6$ group with $Z^5$ being a H atom, an alkyl group, a substituted alkyl group, an acyl group or a substituted acyl group, and $Z^6$ being a H atom, an alkyl group or a substituted alkyl group, and $G^9$ is an O or S atom or an —N=N— group.

Further, the invention concerns a compound having general formula III where the symbols have the following meaning:

P—Q is a C,C double bond or an epoxide,

R is a H atom or a methyl group, $G^{10}$ is an N atom or a $CZ^{12}$ group with $Z^{12}$ being a H atom or halogen atom, an alkyl group, a substituted alkyl group, an aryl group, or a substituted aryl group.

Further, the invention concerns a compound having general formula IV where the symbols have the following meaning:

P—Q is a C,C double bond or an epoxide,

R is a hydrogen atom or a methyl group, and $G^{11}$ is a $H_2N$ group, a substituted $H_2N$ group, an alkyl group, a substituted alkyl group, an aryl group or a substituted aryl group.

Further, the invention concerns an antifungal agent containing or consisting of a compound according to the invention, in addition to an optional carrier, diluent or additive.

Further, the invention concerns a therapeutic agent for the treatment of tumor diseases and growth disturbances, containing or consisting of a compound according to the invention, in addition to an optional carrier, diluent or additive.

DETAILED DESCRIPTION OF THE INVENTION

Definitions

Listed below are definitions of various terms used to describe this invention. These definitions apply to the terms as they are used throughout this specification, unless otherwise limited in specific instances, either individually or as part of a larger group.

The term "pharmaceutically active agent" or "pharmaceutically active epothilone" refers to an epothilone that is pharmacologically active in treating cancer or other diseases described herein.

The term "alkyl" refers to optionally substituted, straight or branched chain saturated hydrocarbon groups of 1 to 20 carbon atoms, preferably 1 to 7 carbon atoms. The expression "lower alkyl" refers to optionally substituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "acyl" refers to a radical derived usually from an acid by removal of the hydroxyl. Examples include acetyl ($CH_3CO$—), benzoyl ($C_6H_5CO$—) and phenylsulfonyl ($C_6H_5SO_2$—)

The term "substituted acyl" refers to a substituted acyl group in which the radical derived usually from an acid by removal of the hydroxyl is substituted by, for example, alkyl, substituted alkyl, cycloalkyl, substituted cycloalkyl, aryl, substituted aryl, aralkyl, substituted aralkyl and heterocycle.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having 6 to 12 carbon atoms in the ring portion, such as phenyl, naphthyl, biphenyl and diphenyl groups, each of which may be optionally substituted.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "aralkyl" refers to an aryl group bonded directly through an alkyl group, such as benzyl.

The term "substituted alkene" and "substituted alkenyl" refer to a moiety having a carbon to carbon double bond, which can be part of a ring system, with at least one substituent being a lower alkyl or substituted lower alkyl. Other substituents are as defined for substituted alkyl.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "heterocycle," "heterocyclic," and "heterocyclo" include one or more alkyl or substituted alkyl groups as described above or one or more groups described above as alkyl or substituted alkyl substituents. Also included are smaller heterocyclos, such as, epoxides and aziridines.

The term "alkanoyl" refers to —C(O)-alkyl.

The term "substituted alkanoyl" refers to —C(O)-substituted alkyl.

The term "aroyl" refers to —C(O)-aryl.

The term "substituted aroyl" refers to —C(O)-substituted aryl.

The term "trialkylsilyl" refers to —Si(alkyl)$_3$.

The term "aryl dialkylsilyl" refers to —Si(alkyl)$_2$ (aryl).

The term "diaryl alkylsilyl" refers to —Si(aryl)$_2$ (alkyl).

The term "heteroatoms" shall include oxygen, sulfur and nitrogen.

The term "halogen" or "halo" refers to fluorine, chlorine, bromine and iodine.

The compounds of formula I through IV may form salts with alkali metals such as sodium, potassium and lithium, with alkaline earth metals such as calcium and magnesium, with organic bases such as dicyclohexylamine and tributylamine, with pyridine and amino acids such as arginine, lysine and the like. Such salts can be obtained, for example, by exchanging the carboxylic acid protons, if they contain a carboxylic acid, from compounds of formula I through IV with the desired ion in a medium in which the salt precipitates or in an aqueous medium followed by evaporation. Other salts can be formed as known to those skilled in the art.

The compounds of formula I through IV form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g. nitrates, phosphates, borates, tartrates, citrates, succinates, benzoates, ascorbates, salicylates and the like). Such salts are formed by reacting a compound of formula I through IV in an equivalent amount of the acid in a medium in which the salt precipitates or in an aqueous medium followed by evaporation.

In addition, zwitterions ("inner salts") can be formed and are included within the term salts as used herein.

Prodrugs and solvates of the compounds of formula I through IV are also contemplated herein. The term prodrug, as used herein, denotes a compound which, upon administration to a subject, undergoes chemical conversion by metabolic or chemical processes to yield a compound of formula I through IV, or a salt and/or solvate thereof. For example, compounds of formula I through IV may form a carboxylate ester moiety. The carboxylate esters are conveniently formed by esterifying any of the carboxylic acid functionalities found on the disclosed ring structure(s). Solvates of the compounds of formula I through IV are preferably hydrates.

Various forms of prodrugs are well known in the art. For examples of such prodrug delivery derivatives, see:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

The compounds of the invention may exist as multiple optical, geometric, and stereoisomers. While the compounds shown herein are depicted for one optical orientation, included within the present invention are all isomers and mixtures thereof.

Use and Utility

The compounds of the invention are microtubule-stabilizing agents. They are thus useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds of the invention will also inhibit angiogenesis, thereby affecting the growth of tumors and providing treatment of tumors and tumor-related disorders. Such anti-angiogenesis properties of the compounds of formula I through IV will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds of the invention will induce or inhibit apoptosis, a physiological cell death process critical for normal development and homeostasis. Alterations of apoptotic pathways contribute to the pathogenesis of a variety of human diseases. Compounds of formula I through IV, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, compounds of the invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The present invention thus provides a method of treating a subject, preferably mammals and especially humans, in need of treatment for any of the aforementioned conditions, especially cancer or other proliferative diseases, comprising the step of administering to a subject in need thereof of at least one compound of formula I through IV in an amount effective therefor. Other therapeutic agents such as those described below may be employed with the inventive compounds in the present method. In the method of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.05 to 200 mg/kg/day, which may be administered in a single dose or in the form of individual divided doses, such as from 1 to 4 times per day. Preferably the compounds are administered in a dosage of less than 100 mg/kg/day, in a single dose or in 2 to 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The present invention also provides a pharmaceutical composition comprising at least one of the compounds of formula I through IV capable of treating cancer or other proliferative diseases in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of formula I through IV may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as a tablet, capsule, solution or suspension containing about 5 to about 500 mg per unit dosage of a compount or mixture of compounds of formula I and II or in a topical form (0.01 to 5% by weight compound of formula I and II, one to five treatments per day). They may be compounded in a conventional manner with a physiologically acceptable vehicle or carrier, excipient, binder, preservative, stabilizer, flavor, etc., or with a topical carrier. The compounds of formula I through IV can also be formulated in compositions such as sterile solutions or suspensions for parenteral administration. About 0.1 to 500 mg of a compound of formula I through IV may be compounded with a physiologically acceptable vehicle, carrier, excipient, binder preservative, stabilizer, etc., in a unit dosage form as called for by accepted pharmaceutical practice. The amount of active sustance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parentally acceptable diluents or solvents, such as cremophor, mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperature, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat plaques associated with psoriasis and as such may be formulated as a cream or ointment.

The compounds of the invention may be administered either alone or in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g. S phase, than the present compounds of formula I through IV which exert their effects at the $G_2$-M phase. Examples for classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A–F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253, and WO 00/00485; cyclin dependent kinase inhibitors as found in WO 99/24416; and prenyl-protein transferase inhibitors as found in WO 97/30992 and WO 98/54966.

The combinations of the present invention may also be formulated or co-administered with other therapeutic agents that are selected for their particular usefulness in administering therapies associates with the aforementioned conditions. For example, the compounds of the invention may be formulated with agents to prevent nausea, hypersensitivity, and gastric irritation, such as antiemetics, and $H_1$ and $H_2$ antihistaminics.

The above therapeutic agents, when employed in combination with the compounds of the present invention, may be used in those amounts indicated in the Physicians' Desk Reference (PDR) or as otherwise determined by one of ordinary skill in the art.

General Methods of Preparation
(A) Epothilone Derivatives I to III

The present invention is directed to the preparation of epothilone derivatives Ia, Ib, IIa, IIb and III in which the hydrogen atoms of the C-21 methyl group have been substituted partially or completely by other groups $G^1$ to $G^{11}$. R can be a hydrogen or methyl, P—Q a C,C double bond or an epoxide.

The following general formula shows the epothilone core including the —CH= group at position 17 (C17 carbon atom) whereas formulae Ia, Ib, IIa, IIb, and III refer to compounds having said epothilone core plus one of the substituents shown in combination with the symbols of these compounds Ia, Ib, IIa, IIb, and III.

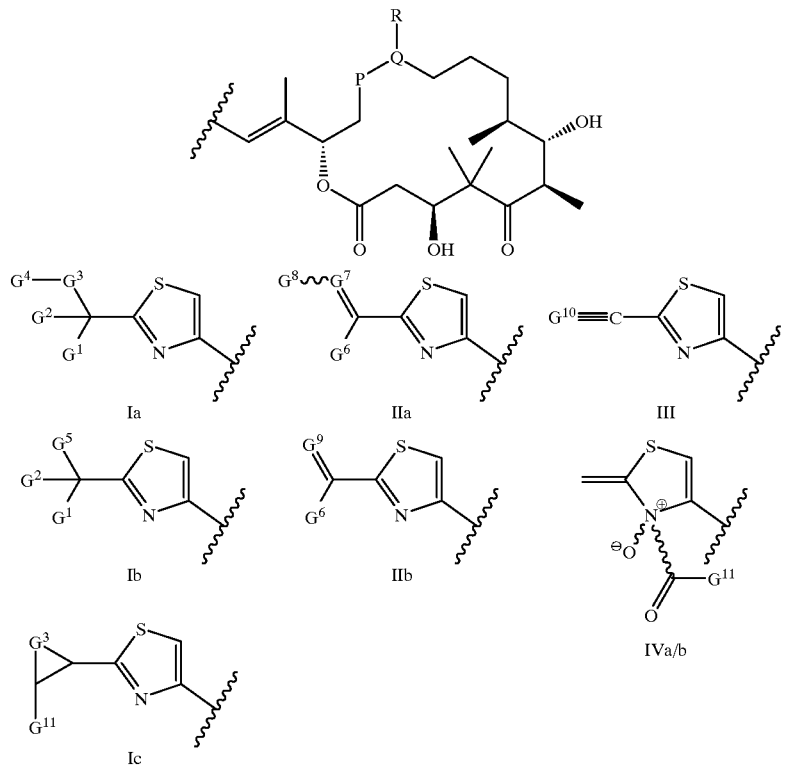

$G^1$=H, halogen, CN, alkyl, substituted alkyl
$G^2$=H, alkyl, substituted alkyl
$G^3$=O, S, $NZ^1$
$G^4$=H, alkyl, substituted alkyl, $OZ^2$, $NZ^2Z^3$, $Z^2C=O$, $Z^4$ $SO_2$, optionally substituted glycosyl
$G^5$=halogen, $N_3$, NCS, SR, CN, NC, $N(Z^1)_3^+$, heteroaryl G⁶=H, alkyl, substituted alkyl, CF₃, OZ⁵, SZ⁵, NZ⁵Z⁶
G⁷=CZ⁷, N
G⁸=H, halogen, alkyl, substituted alkyl, OZ¹⁰, SZ¹⁰, NZ¹⁰Z¹¹
G⁹=O, S, —NH—NH—, —N=N—
G¹⁰=N, CZ¹²
G¹¹=H₂N, substituted H₂N, alkyl, substituted alkyl, aryl, substituted aryl
Z¹=H, alkyl, substituted alkyl, acyl, substituted acyl
Z²=H, alkyl, substituted alkyl, aryl, substituted aryl, heterocycle
Z³=H, alkyl, substituted alkyl, acyl, substitued acyl, aryl, substituted aryl
Z⁴=alkyl, substituted alkyl, aryl, substituted aryl, heterocycle
Z⁵=H, alkyl, substituted alkyl, acyl, substituted acyl, aryl, substituted aryl
Z⁶=H, alkyl, substituted alkyl, acyl, substituted acyl
Z⁷=H, halogen, alkyl, substituted alkyl, aryl, substituted aryl, OZ⁸, SZ⁸, NZ⁸Z⁹
Z⁸=H, alkyl, substituted alkyl, acyl, substituted acyl, aryl, substituted aryl
Z⁹=H, alkyl, substituted alkyl, acyl, substituted acyl
Z¹⁰=H, alkyl, substituted alkyl, acyl, substituted acyl, aryl, substituted aryl
Z¹¹=H, alkyl, substituted alkyl, acyl, substituted acyl
Z¹²=H, halogen, alkyl, substituted alkyl, aryl, substituted aryl Compounds of the invention can be prepared from compounds and by the general methods described in the following schemes 1 to 8. All substituents are as defined in the schemes that follow or as defined above.

Starting from the unprotected 3,7-hydroxy or, for example, TMS-protected epothilones A–C (1), 21-hydroxyepothilones (4) can be obtained from the N-oxides (2) the preparation of which is described in WO 98/38192 and incorporated herein as if set forth at length (scheme 1). The N-oxides (2) are reacted with acid halides and bases, preferably p-toluenesulfonic acid halides and 2,6-lutidine, to give the 21-haloepothilones (3). Deoxygenation of the epoxides (4) according to known methods yields the 21-hydroxyepothilones C and D (5).

Alternatively, (4) and (5) can be obtained by biotransformation (21-hydroxylation) of epothilones A–D with the aid of, for example, *Sorangium cellulosum* strains as described in WO 98/22461 or by Actinomyces sp. strain 15847 as described in PCT/US99/27954 which are incorporated by reference as if set forth at length. The 3,7-OH protected or unprotected epothilone 3, 4, 5 (scheme 1) (see, for example, WO 97/19086) will serve in the following for the preparation of the derivatives of structural types I–III.

Scheme 1

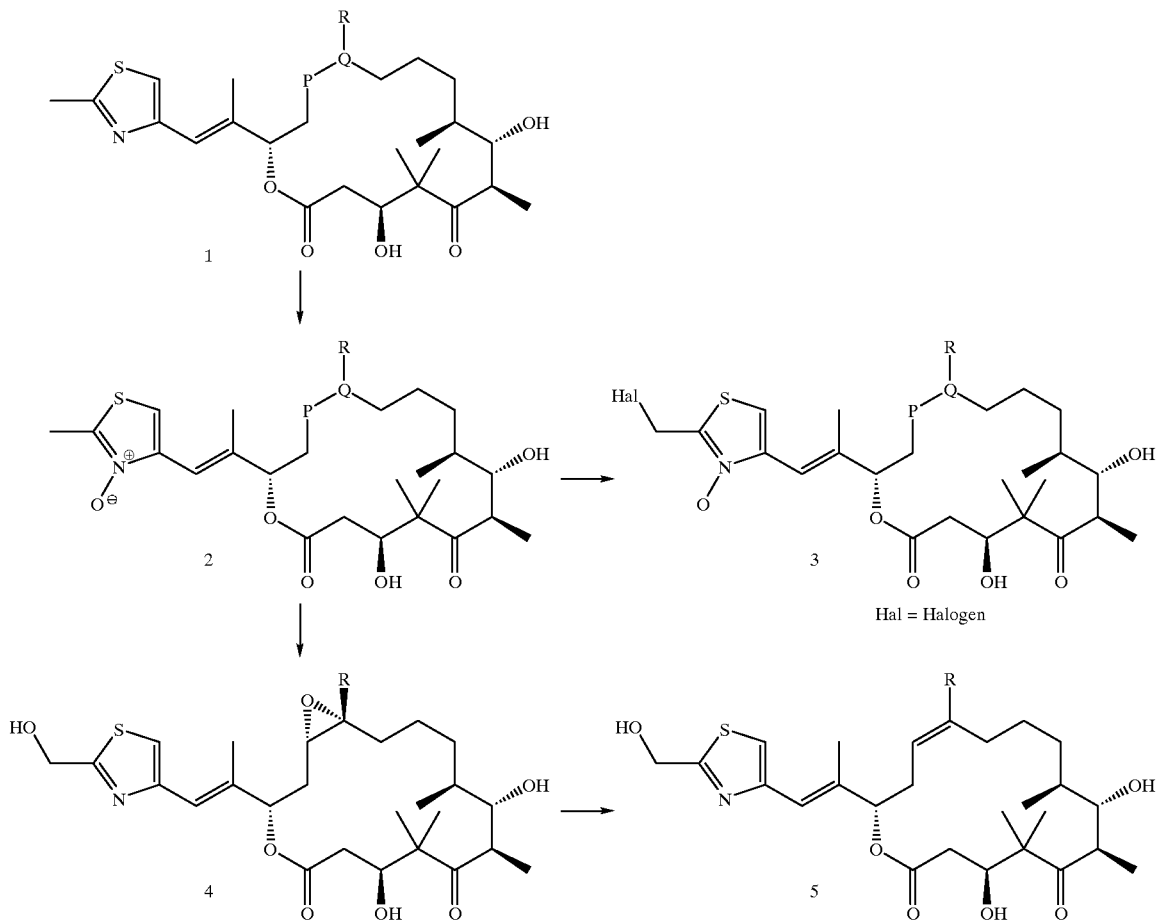

Scheme 2 can be illustrated as follows (an omitted epothilone core including the —CH= group at position 17 means that this part of the molecule has not been involved in the reactions as illustrated).

where $R^1$ can be optionally substituted alkyl, acyl, optionally substituted aryl-sulfonyl or optionally substituted glycosyl for the preparation of compound (6), alkyl or acyl for the preparation of compounds (8) or (10). If compound 9 is

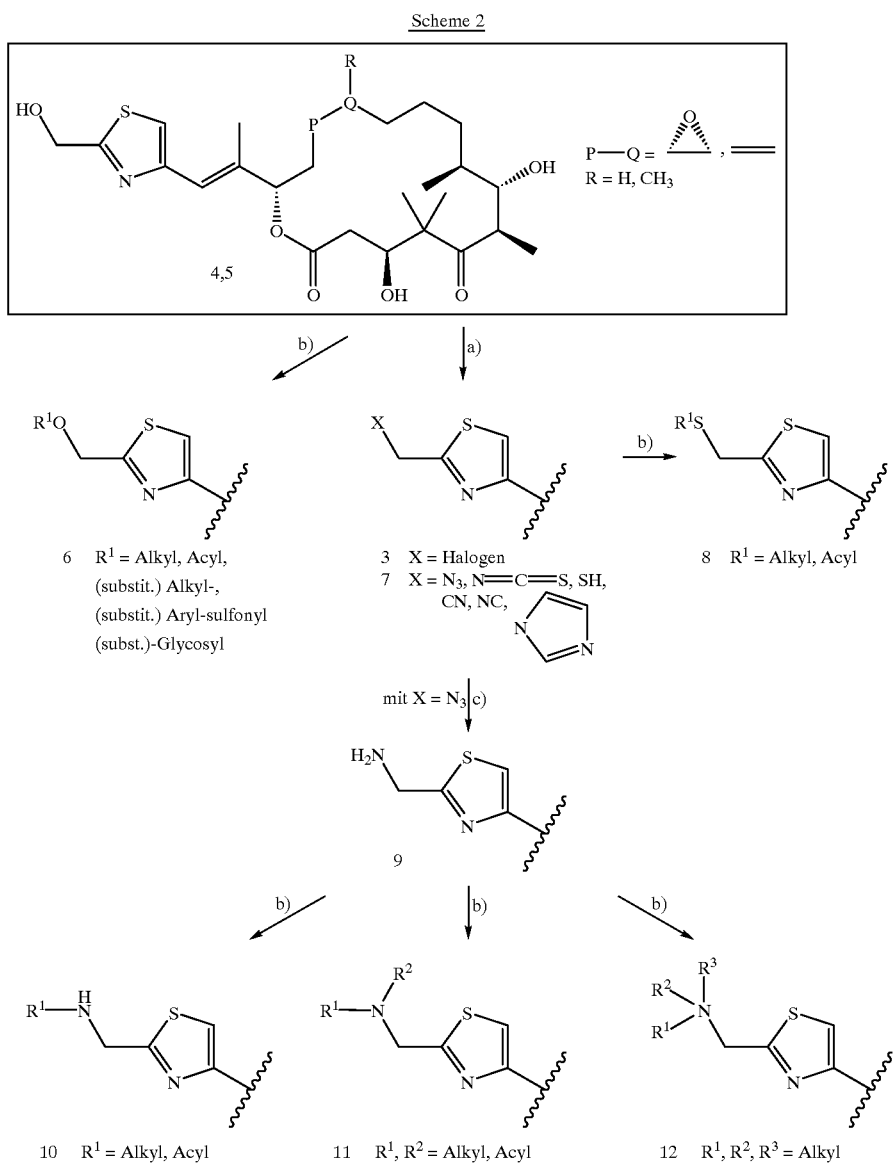

a) Compounds 3 and 7 can be obtained from compounds 4 or 5 by i) an activation, for example, with TosHal/pyridine, followed by ii) a nucleophilic displacement with halide anions (compound 3) $N_3$, N=C=S, CN, NC or SH anions (compound 7) for OH; $NaN_3$ is, for example, used to introduce $N_3$ and AgCN, for example, to introduce an isonitrile group.

b) Compound 6 can be obtained from compound 4 or 5, compound 8 from compound 3 or 7 (X=SH), and compound 10 from compound 9 by reacting the starting compound with an agent of the formula $R^1Hal$ in the presence of a base, reacted with agents of the formulae $R^1Hal$ and $R^2Hal$ ($R^1$ and $R^2$=alkyl or acyl), compound 11 results; and if compound 9 is reacted with agents of formulae $R^1Hal$, $R^2Hal$ and $R^3Hal$ ($R^1$, $R^2$ and $R^3$=alkyl), compound 12 results.

c) Compound 9 can be obtained from compound 7 for $X=N_3$ by i) reduction e.g. with $H_2$ and Lindlar catalyst/EtOH or ii) or with phosphines, e.g. $PMe_3$ followed by $NH_3$ aq.

Scheme 3 can be illustrated as follows (an omitted epothilone core including the —CH= group at position 17 means that this part of the molecule has not been involved in the reaction as illustrated).

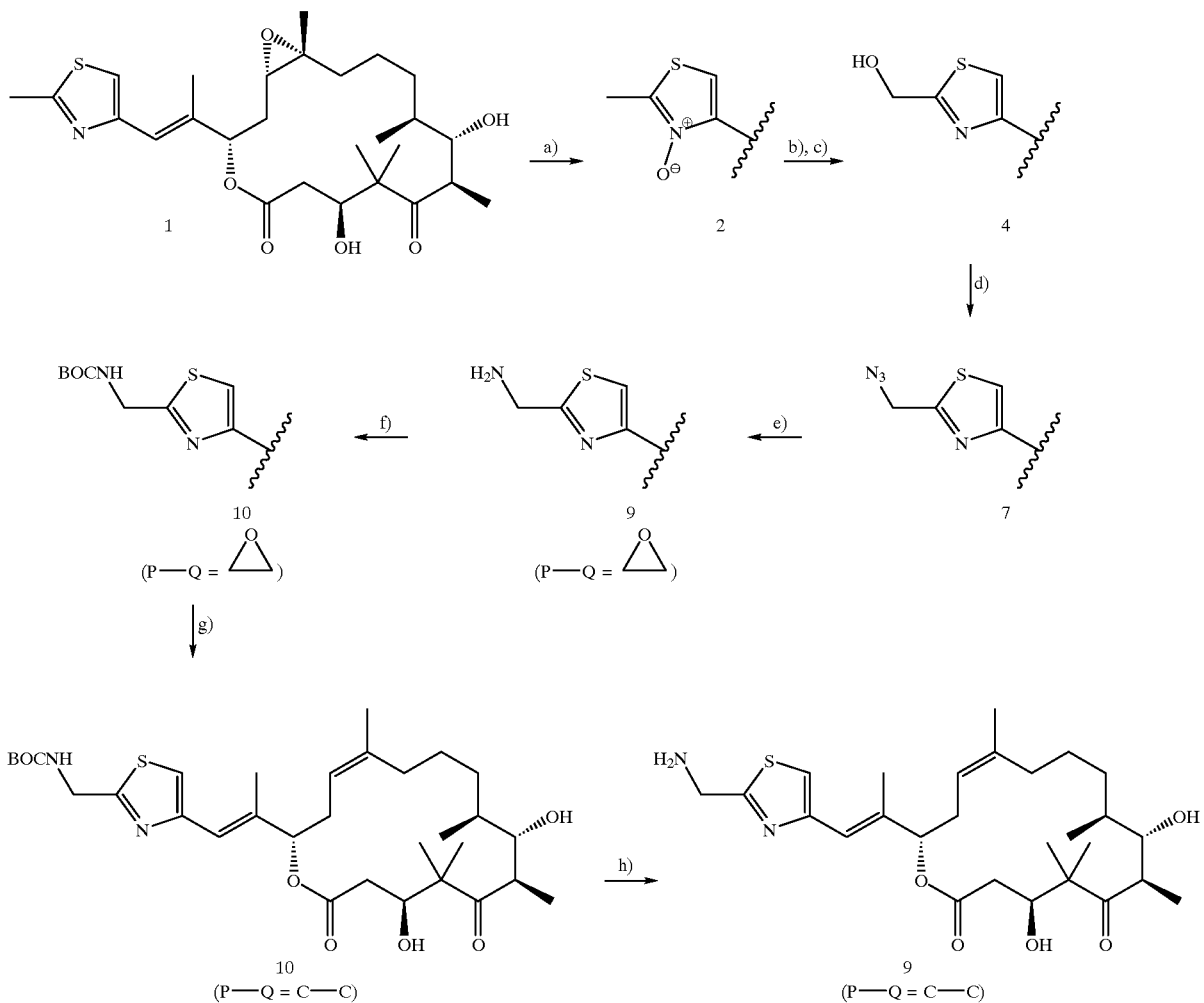

Scheme 3 a) Compound 2 can be obtained by reacting compound 1 with an oxygenating agent, such as, m-chloroperbenzoic acid.

b) and c) Compound 4 can be obtained by reacting compound 2 with (b) an acylating system comprising, e.g. (b) (CF$_3$CO)$_2$O/2,6-lutidine followed by (c) MeOH/NH$_3$aq.

d) Compound 7 can be obtained by reacting compound 4 with diphenylphosphoryl azide (DPPA)/ diazabicycloundecene (DBU).

e) Compound 9(P—Q=epoxide) can be obtained by reduction of compound 7 with a phosphine, e.g. PME$_3$ followed by NH$_3$ aq.

f) Compound 10 with P—Q=epoxide can be obtained by reacting compound 9 with (tBuOCO)$_2$O/NEt$_3$.

g) Compound 10 with P—Q=C=C double bond can be obtained by reduction of compound 10 with P—Q=epoxide using WCl$_6$/nBuLi.

h) Compound 9(P—Q=double bond) can be obtained by deprotection of compound 10 with P—Q=C=C double bond and R$^1$=tBuOCO using trifluoroacetic acid (TFA).

Scheme 4 can be illustrated as follows (an omitted epothilone core including the —CH= group at position 17 means this part of the molecule has not been involved in the reaction as illustrated).

Scheme 4

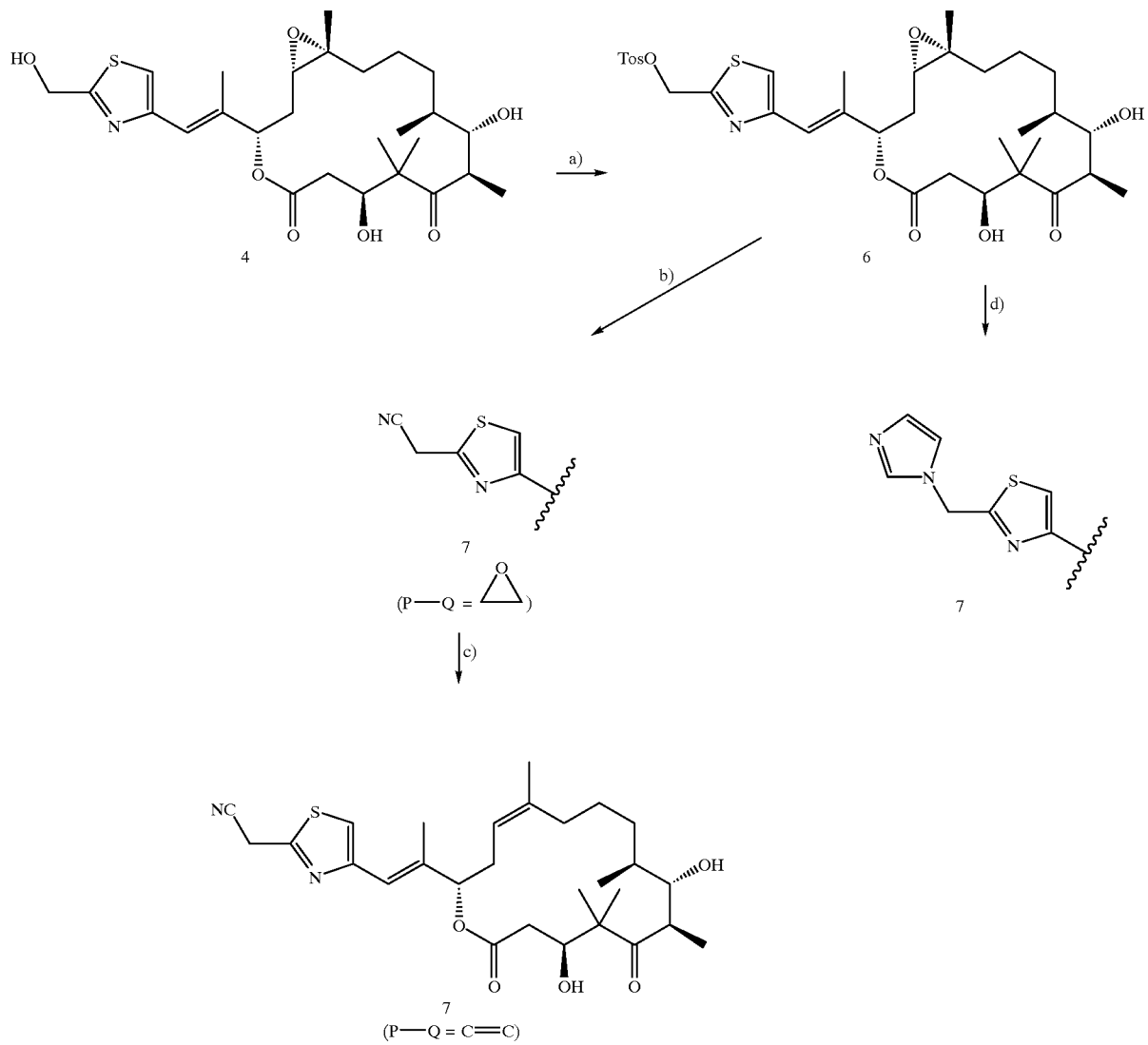

a) Compound 6 can be obtained from compound 4 by acylation with p-tosylchloride/Hunig base.

b) Compound 7 with unchanged epoxide can be obtained from compound 6 by substitution with cyanide, e.g. KCN/18-crown-6.

c) Compound 7 with P—Q=C=C double bond can be obtained from compound 7 with P—Q=epoxide by reduction using $WCl_6$/nBuLi.

d) Compound 7 with unchanged epoxide can be obtained from compound 6 by substitution with imidazole in presence of base, e.g. $K_2CO_3$ Scheme 5 can be illustrated as follows (an omitted epothilone core including the —CH= group at position 17 means this part of the molecule has not been involved in the reaction as illustrated).

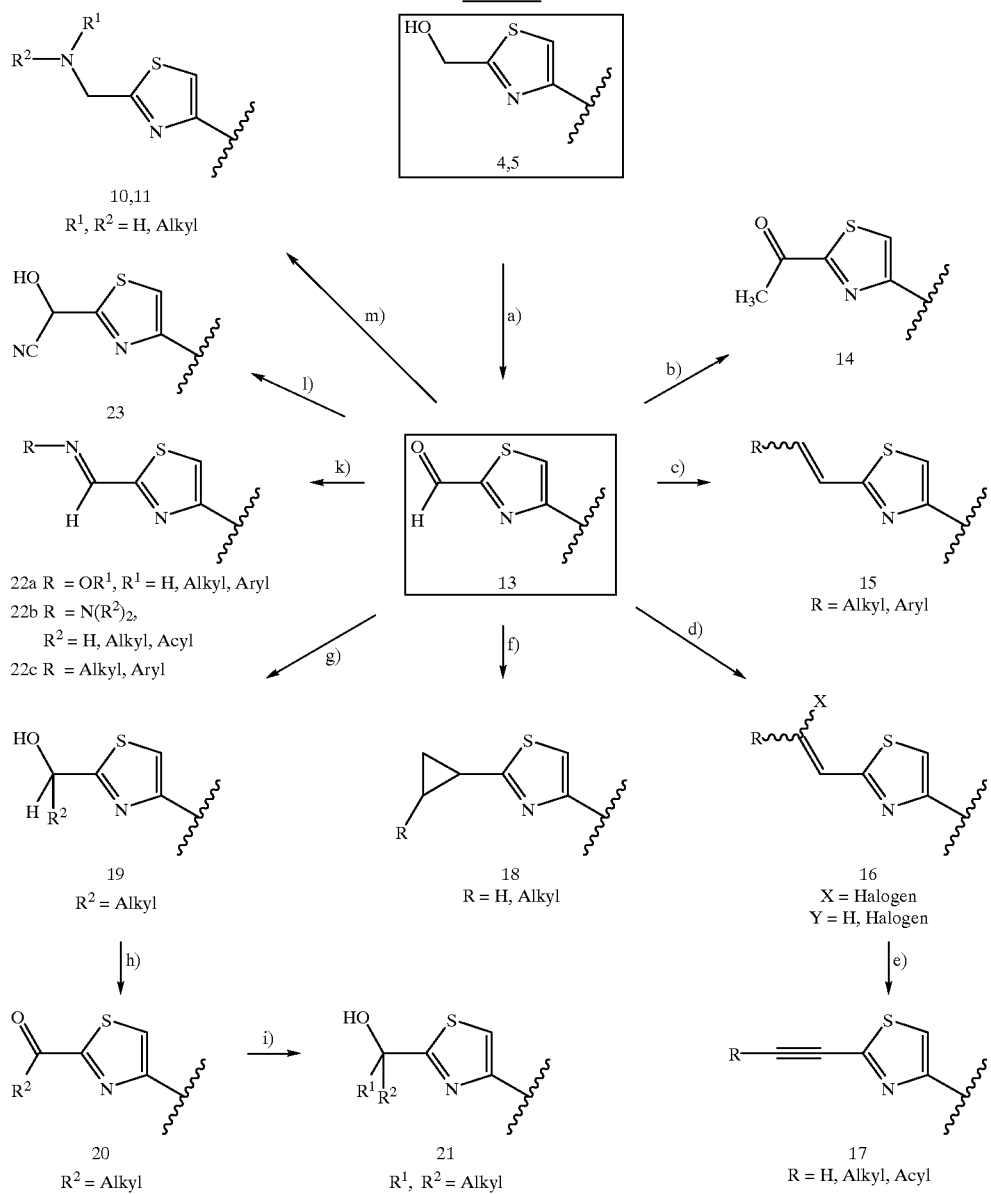

a) Compound 13 can be obtained by oxidation of compound 4 or 5 with e.g. $MnO_2$.

b) Compound 14 can be obtained by reacting compound 13 with $CH_2N_2$.

c) Compound 15 can be obtained by subjecting compound 13 to a Wittig type reaction.

d) Compound 16 can be obtained by treating compound 13 with a reaction system comprising $CrCl_2$ and $CHHal_3$.

e) Compound 17 can be obtained by reacting compound 16 with BuLi and RHal (R=H, alkyl or acyl).

f) Compound 18 can be obtained by reacting compound 13 with $CH_2N_2$ for 18 (R=H on the C21 substituent) or $Me_2SOCHR$ for 18 (R=H, alkyl).

g) Compound 19 can be obtained by reacting compound 13 with $R^2MgHal$ or $R^2Li$ ($R^2$=alkyl).

h) Compound 20 can be obtained by oxidising compound 19 with e.g. $MnO_2$.

i) Compound 21 can be obtained by reacting compound 20 with $R^1MgHal$ or $R^1Li$ ($R^1$=alkyl)

k) Compound 22a, 22b or 22c can be obtained by reacting compound 13 with $H_2NR$, where $R=OR^1$ and $R^1$=hydrogen, alkyl or aryl for compound (22a); $R=N(R^2)_2$ and $R^2$=hydrogen, alkyl or acyl for compound (22b) and R=alkyl or aryl for compound 22c.

l) Compound 23 can be obtained by reacting compound 13 with a CN source, e.g. HCN.

m) Compounds 10 and 11 can be obtained by reductive amination of 13 with $HNR^1R^2$ and e.g. $NaBH_3CN$, where $R^1$ and $R^2$=H, alkyl.

Scheme 6 can be illustrated as follows (an omitted epothilone core including the —CH═ group at position 17 means that this part of the molecule has not been involved in the reaction as illustrated).

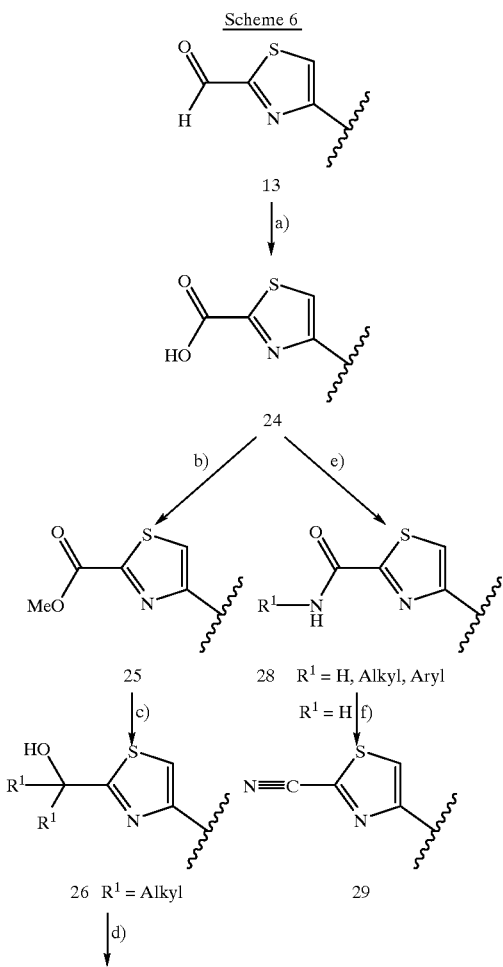

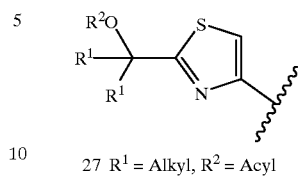

27 $R^1$ = Alkyl, $R^2$ = Acyl a) Compound 24 can be obtained by oxidising compound 13 with e.g. $Ag_2O$ in THF/water (THF/water ratio, for example, 9:1).

b) Compound 25 can be obtained by methylating compound 24 with e.g. $CH_2N_2$ in ethyl acetate.

c) Compound 26 can be obtained by reaction of compound 25 with excess $R^1MgHal$ or $R^1Li$ ($R^1$=alkyl).

d) Compound 27 can be obtained by acylating compound 26 with $R^2Hal$ ($R^2$=acyl) in the presence of a base, e.g. DMAP.

e) Compound 28 can be obtained by first activation of the carboxy group in 24 with e.g. ethyl chlorofarmate/$NEt_3$ and second reaction with $R^1NH_2$ ($R^1$=hydrogen, alkyl or aryl) in THF.

f) Compound 29 can be obtained by dehydration of compound 28 ($R^1$ hydrogen) with e.g. $POCl_3$/$NEt_3$.

Scheme 7 can be illustrated as follows (an omitted epothilone core including the —CH═ group at position 17 means that this part of the molecule has not been involved in the reaction as illustrated).

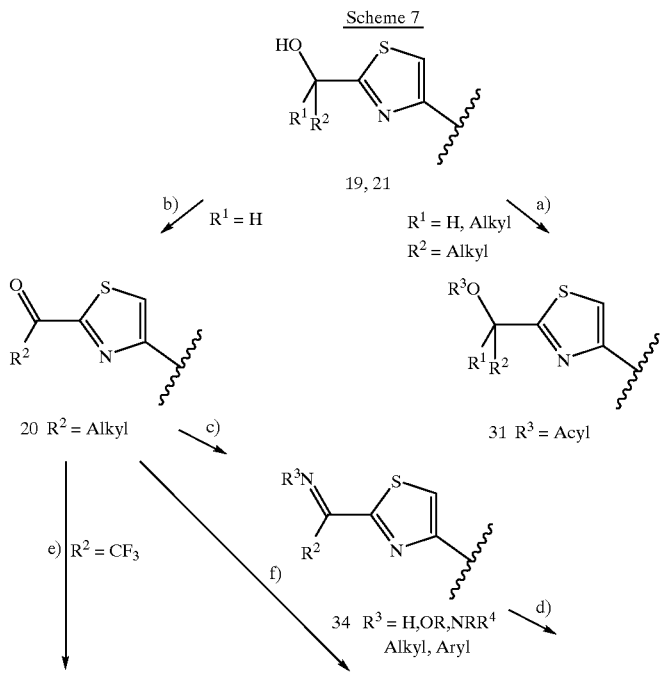

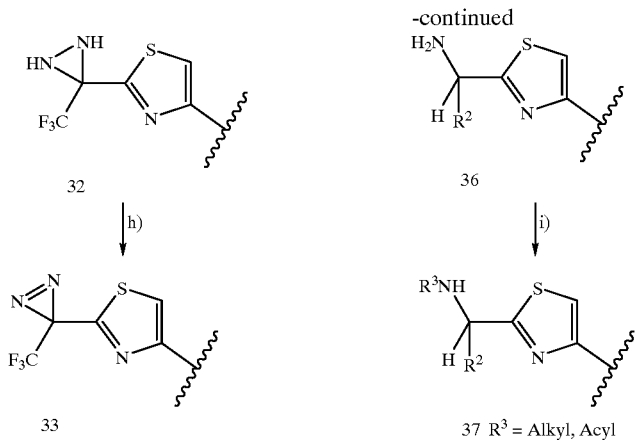
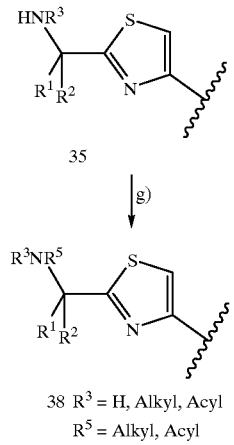

a) Compound 31 ($R^3$=acyl) can be obtained by reacting compound 19 or 21 with an activated carboxylic acid derivative, e.g. RCOHal ($R^3$=RCO) in the presence of a base.

b) Compound 20 can be obtained by oxidising compound 19 ($R^1$=hydrogen, $R^2$=alkyl) with e.g. $MnO_2$.

c) Compound 34 can be obtained by condensation of compound 20 with $H_2NR^3$ ($R^3$=hydrogen, alkyl, aryl OR or $NRR^4$ with R and $R^4$=alkyl, aryl).

d) Compound 35 can be obtained by reacting compound 34 ($R^3$=alkyl, aryl) with $R^1$MgHal or $R^1$Li (R1 and R2=alkyl).

e) Compound 32 can be obtained by reacting compound 20 ($R^2=CF_3$) with i) $H_2$NOpTos and ii) $NH_3$ (fl.).

f) Compound 36 can be obtained by subjecting compound 20 to a reductive amination.

g) Compound 38 can be obtained by alkylating or acylating compound 35 with $R^5$Hal ($R^5$=alkyl or acyl) in the presence of a base.

h) Compound 33 can be obtained by oxidation of compound 32 with e.g. $Ag_2O$.

i) Compound 37 can be obtained by alkylating or acylating compound 36 with $R^3$Hal ($R^3$=alkyl or acyl) in the presence of a base.

(B) Epothilone Derivatives IV

Further, the invention is directed to the preparation of epothilone derivatives IV having the foregoing formula IV where the symbols have the following meaning:

P—Q is a C,C double bond or an epoxide,

R is a H atom or a methyl group, and $G^{11}$ is a $H_2N$ group, a substituted $H_2N$ group, an alkyl group, a substituted alkyl group, an aryl group or a substituted aryl group.

Preparation and Rearrangement of N-Acylepothilone-N-oxides

The production of epothilone-N-oxides (2) (P—Q=epoxide) and their rearrangement to 21-acyloxyepothilone of the following formula 6 has been described in WO 98/38192, the full text of which is incorporated herein by reference.

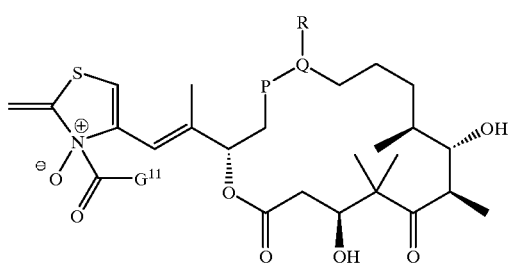

IV

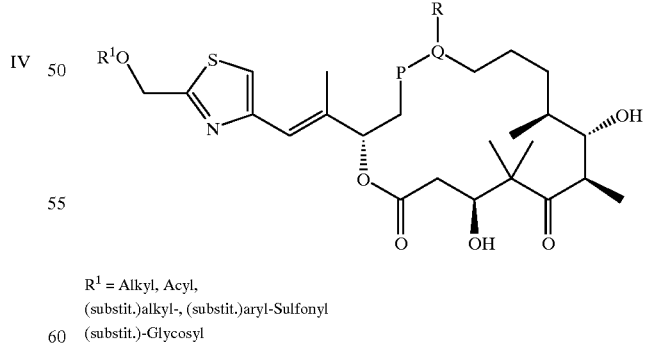

$R^1$ = Alkyl, Acyl,
(substit.)alkyl-, (substit.)aryl-Sulfonyl
(substit.)-Glycosyl Scheme 8

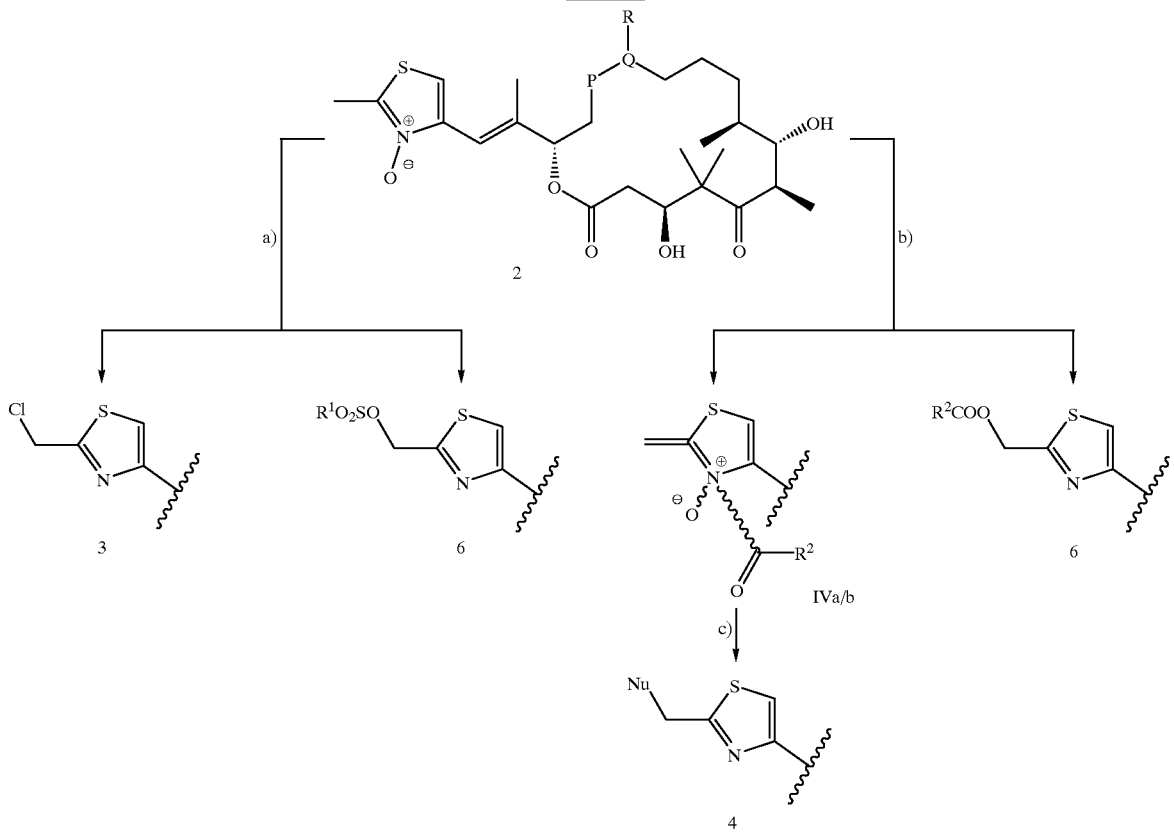

Scheme 8 can be illustrated as follows (an omitted epothilone core including the —CH═ group at position 17 means that this part of the molecule has not been involved in the reaction as illustrated). P—Q represents an epoxide or a C,C double bond, R is a hydrogen atom or a methyl group.

a) Compounds 3 and 6 can be obtained by reacting compound 2 with $R^1SO_2Cl$ in the presence of a base ($R^1$=optionally substituted alkyl or optionally substituted aryl).

b) Compounds 6 and IVa/b can be obtained by reacting compound 2 with an activated carboxylic acid derivative, e.g. carboxylic acid anhydride.

c) Compound 4 can be obtained by reacting compound IVa/b with a nucleophile NuH or Nu$^-$.

The esters 6 are useful intermediate products for a great number of epothilones which have been further modified at position C-21.

For example, if 2 is reacted with for example, acetic anhydride, a new unexpected intermediate compound IV can be found after a short reaction period, whereas IV is completely transformed to 6 after a longer reaction period. If the reaction is interrupted at a proper point in time, IV can be isolated chromatographically as two diastereomers IVa and IVb.

Compounds of type IV have not yet been described. The structure can clearly be derived from their spectroscopical data and their subsequent reactions.

For preparative purposes their reaction with nucleophiles leading to C-21 substituted epothilones 6 is of special importance; Nu=for example carbon-, nitrogen-, oxygen-, sulfur- and halogen-substituents.

EXAMPLES

The following non-limiting examples serve to illustrate the practice of the invention.

Example 1

Conversion of Epothilone B to Epothilone F

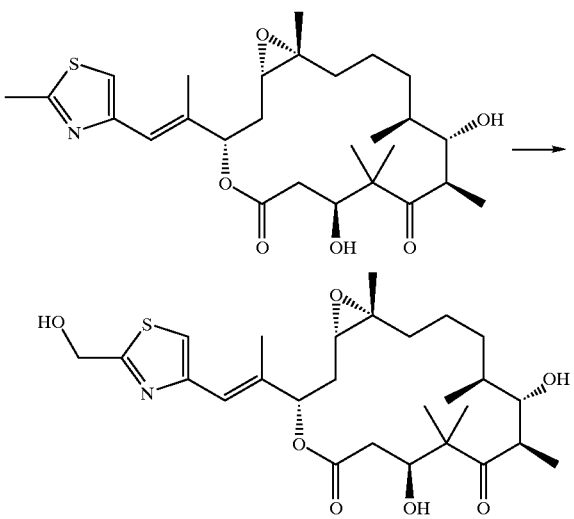

(i) 1.98 g (3.90 mmol) of Epothilone B was placed under Argon and dissolved in 60 mL dry $CH_2Cl_2$. To this solution was added 0.720 g mCPBA (4.17 mmol, 1.07 equivalents). The mixture was allowed to stir at 25° C. for 5.5 hours. The reaction mixture was quenched with 60 mL NaHCO$_3$, and extracted with 3×75 mL of CHCl$_3$. The organic phase was washed with 100 mL water followed by 70 mL of 5% Na$_2$SO$_{3(aq)}$ and then 70 mL brine. The organic phase was then dried over Na$_2$SO$_4$. The crude reaction product was chromatographed using silica gel eluting with 2% MeOH in CHCl$_3$ to yield 0.976 g of the N-oxide (48%) as a white fluffy solid.

(ii) To a resealable tube under Argon was added 0.976 g of the N-oxide (1.86 mmol) dissolved in 35 mL dry CH$_2$Cl$_2$, 2,6-lutidine (1.73 mL, 14.88 mmol, 8 equivalents) and (CF$_3$CO)$_2$O (1.84 mL, 13.02 mmol, 7 equivalents). The tube was sealed and heated at 70° C. for 25 min. The mixture was allowed to cool and the solvent was removed under a stream of argon, followed by concentration to a few mL of dark yellow solution under vacuum. The reaction was diluted with 25 mL MeOH and 2.9 mL of 28% NH$_4$OH$_{(aq)}$ was added. The mixture was heated to 45° C. for 20 min, then cooled to room temperature. The crude product was concentrated on the rotary evaporator and chromatographed using silica gel eluting with 4% MeOH in CHCl$_3$ to yield 0.815 g of Epothilone F (84%).

Example 2

Synthesis of 21-azido-epothilones 7
Example: [1S-[1R*,3R* (E),7R*, 10S*,11R*,12R*,16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5,9-dione (R=CH$_3$, G$^1$=G$^2$=H, G$^5$=N$_3$ in formula Ib)

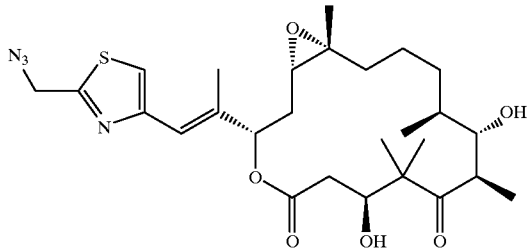

To a stirred solution of epothilone F from Example 1 above (957 mg, 1.83 mmol) in 20.0 mL tetrahydrofuran at 0° C. under Argon was added 0.47 mL diphenylphosphoryl azide (604 mg, 2.19 mmol, 1.2 equivalents). The mixture was stirred for approximately 3 min. 1,8-diazabicyclo[5.4.0]undec-7-ene (0.27 mL, 278 mg, 1.83 mmol, 1 equivalents) was then added and the mixture was stirred at 0° C. After 2 hours, the mixture was warmed to 25° C. and stirred for 20 hours. The reaction mixture was diluted with 150 mL ethyl acetate and washed with 50 mL H$_2$O. The aqueous layer was extracted with 35 mL ethyl acetate. The combined organic layers were dried over Na$_2$SO$_4$ and concentrated under vacuum. The crude material was chromatographed using silica gel eluted with 50% ethyl acetate in hexanes to afford 913 mg (91%) of 21-azido-epothilone B, as a clear, colorless oil. MS (ESI$^+$): 549.3 (M+H)$^+$; $^1$H-NMR (300 MHz, CDCl$_3$); δ=6.59 (bs, 17-H), 7.04 (s, 19-H), 4.63 (s, 21-H$_2$); HRMS (DCI); C$_{27}$H$_{40}$N$_4$O$_6$S: [M$^+$] calculated 549.2747, found 549.2768.

Example 3

Synthesis of 21-amino-epothilones 9
Example: [1S-[1R*,3R*(E),7R*, 10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (R=CH$_3$, G$^1$=G$^2$=G$^4$=Z$^1$=H, G$^3$=NZ$^1$ in formula Ia)

Lindlar catalyst, 18.0 mg, was suspended in 500 μL of ethanol in an H$_2$ atmosphere and was saturated. Then, 15.9 mg (29.0 μmol) of 21-azido-epothilone B from Example 2 above, dissolved in an ethanol-methanol mixture, was added. After stirring for 30 minutes at room temperature, the suspension is filtered through Celite, and washed with ethyl acetate. The solvent was removed from the organic phase and dried in high vacuum. The purification of the crude product was done through PSC (solvent: CH$_2$Cl$_2$/methanol 90:10), whereupon 12.3 mg (81%) of 21-amino-epothilone B and 1 mg (6%) of educt is obtained.

$^1$H-NMR (300 MHz, CDCl$_3$); δ=6.58 (bs, 17-H), 7.05 (s, 19-H), 4.15 (s, 21-H$_2$); HRMS (DCI); C$_{27}$H$_{42}$N$_2$O$_6$S: [M+H$^+$] calculated 522.2764, found 522.2772.

Example 4

Synthesis of 21-amino-epothilones 9 (alternative)

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione

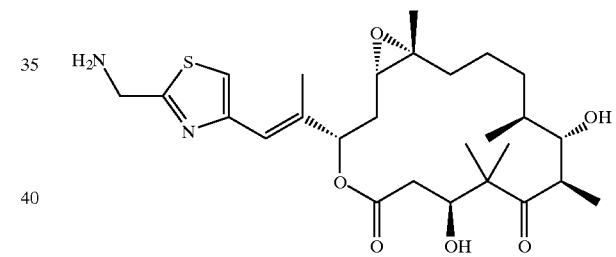

To a stirred solution of 21-azido-epothilone B (Example 2) (1.070 g, 1.950 mmol) in 30.0 mL tetrahydrofuran under Argon was added 0.22 mL of trimethylphosphine (0.163 g, 2.145 mmol, 1.1 equivalents). H$_2$O (5.5 mL) was then added, and the mixture was allowed to stir at 25° C. After 3 hours, the azide was completely consumed and 3 mL of 28% aqueous NH$_4$OH$_{(aq)}$ was added to complete the conversion of phosphoryl imine to amine. After stirring at 25° C. for 1 hour the solvents were removed under vacuum. The crude material was chromatographed using silica gel eluted with 1% Et$_3$N, 2.5% MeOH in CHCl$_3$ to yield 924 mg (91%) of 21-amino-epothilone B, as a white solid. MS (ESI$^+$): 523.3 (M+H)$^+$.

Example 5

[1S-[1R*,3R*(E),7R*,10S*,11R*,12R*,16S*]]-3-[2-[2-[[[(1,1-Dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione

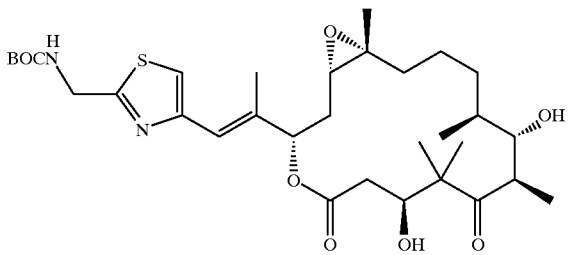
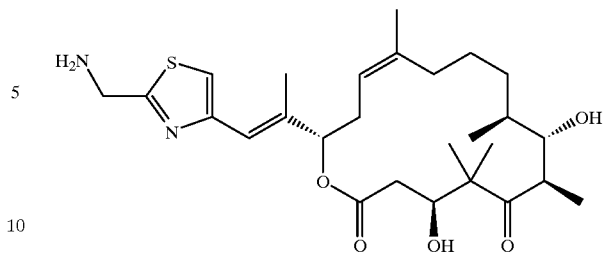

To a solution of 21-amino-epothilone B (126 mg, 0.24 mmol) in methanol (4.0 mL) was added triethylamine (67 μL, 0.48 mmol, 2 equivalents) and di-t-butyl-dicarbonate (65 mg, 0.3 mmol, 1.25 equivalents). The reaction mixture was stirred for 2 hours. TLC indicated loss of starting material. The reaction mixture was concentrated in vacuo and chromatographed on silica gel with 5% MeOH in CHCl$_3$ as eluent to provide 164 mg (100%) of 21-amino-epothilone B as a white solid.

Example 6

[4S-[4R*,7S*,8R*,9R*,15R*(E)]]-16-[2-[2-[[[(1,1-Dimethylethoxy)carbonyl]amino]methyl]-4-thiazolyl]-1-methyl-ethenyl]-4,8-dihydroxy-5,5,7,9,13-pentamethyl-1-oxa-13(Z)-cyclohexadecene-2,6-dione Anhydrous tetrahydrofuran (3.0 mL) was placed in an oven-dried flask under Argon and cooled to −78° C. Under Argon flow, WCl$_6$ (206 mg, 0.52 mmol, 2 equivalents) was added to the cold tetrahydrofuran followed by n-butyllithium (0.650 mL of 1.6 M solution in hexanes, 1.04 mmol 4 equivalents). The reaction flask was removed from the −78° C. cooling bath and stirred at ambient temperature for 15 min. The reaction was then placed into a 0° C. bath and stirred for an additional 5 minutes before adding a solution of 21-amino-epothilone B (azeotroped overnight from toluene in vacuo to dry) (164 mg, 0.26 mmol, 1 equivalents) in tetrahydrofuran (1.5 mL). The reaction was maintained at 0° C. for 45 min. TLC showed the consumption of most of the starting material. The reaction was quenched with saturated aqueous NaHCO$_3$ (5 mL) and partitioned between saturated aqueous NaHCO$_3$ (25 mL) and CH$_2$Cl$_2$ (50 mL). The aqueous phase was extracted three times with CH$_2$Cl$_2$. The combined organic layers were dried over Na$_2$SO$_4$, concentrated in vacuo, and purified by chromatography on silica gel first with 7% MeOH in CHCl$_3$, and then by a second column eluted with 50% ethyl acetate in hexanes to obtain 65 mg (41%) of 21-N-BOC-amino-epothilone D. MS (ESI$^+$): 607.3 (M+H)$^+$; MS (ESI$^-$): 605.3 (M−H)$^-$.

Example 7

[4S-[4R*,7S*,8R*,9R*,15R*(E)]]-16-[2-[2-(Aminomethyl)-4-thiazolyl]-1-methylethenyl]-4,8-dihydroxy-5,5,7,9,13-pentamethyl-1-oxa-13(Z)-cyclohexadecene-2,6-dione At 0° C. 21-N-BOC-amino-epothilone D (98 mg, 0.16 mmol) was treated with a pre-cooled solution of 10% trifluoroacetic acid in CH$_2$Cl$_2$ (4.0 mL). After 40 min, the reaction was allowed to warm to ambient temperature, and after an additional 20 minutes neat trifluoroacetic acid (0.6 mL) was added. After 50 minutes more, an additional amount (0.5 mL) of trifluoroacetic acid was added. The reaction was deemed 50% complete 1.75 hours later and the solvents were removed in vacuo. The residue was taken up in ethyl acetate (50 mL) and saturated aqueous NH$_4$OH (50 mL), and extracted with ethyl acetate (3×50 mL). The combined organic layers were dried over Na$_2$SO$_4$, and then chromatographed on silica gel eluting first with neat ethyl acetate followed by 10% MeOH in ethyl acetate with 1% trifluoroacetic acid to obtain 16.8 mg (38%) of the desired 21-amino-epothilone D as a clear film along with 45 mg of 21-N-BOC-amino epothilone D. MS (ESI$^+$): 506.3 (M+H)$^+$; MS (ESI$^-$): 504.3 (M−H)$^-$.

Examples of the synthesis of 21-acyloxy-epothilones 6 are given in Examples 8 to 10.

Example 8

Example: [1S-[1R*,3R*(E),7R*,10S*,11R*,12R*,16S*]]-7,11-Dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione (R=G$^1$=G$^2$=H, G$^3$=O, G$^4$=Z$^2$C═O, Z$^2$=n-Bu in formula Ia)

To a solution of 20 mg (39 F$\mu$mol) epothilone A-N-oxide in 100 μL of CH$_2$Cl$_2$, 83.0 μL (419 μmol) of valeric acid anhydride and 20.0 μL (172 μmol) of 2,6-lutidine were added. The reaction batch was stirred for 30 minutes at 75° C., the solvent was removed and dried in high vacuum. The purification of the crude product was done using preparative HPLC (Nucleosil 100, solvent: CH$_3$CN/H$_2$O 50:50) obtaining 9 mg (40%) of epothilone-E-21 valerate.

$^1$H-NMR (300 MHz, CDCl$_3$); δ=6.60 (s, 17-H), 7.14 (s, 19-H), 5.35 (s, 21-H$_2$), 3.62 (t, 2'-H$_2$), 1.6–1.7 (m, 3'-H$_2$), 1.3–1.4 (m, 4'-H$_2$), 0.91 (t, 5'-H$_3$). HRMS (EI); C$_{31}$H$_{47}$NO$_8$S: calculated 593.3022, found 593.3007.

Example 9

Example: [1S-[1R*,3R*(E),7R*,10S*,11R*,12R*,16S*]]-7,11-Dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione (R=G$^1$=G$^2$=H, G$^3$=O, G$^4$=Z$^2$C═O, Z$^2$=Naphthyl in formula Ia)

Epothilone A-N-oxide, 21 mg (41 μmol), was dissolved in 80 μL CH$_2$Cl$_2$ and 10 μL (86 μmol) of 2,6-lutidine and 82.0 μL (129 μmol) of 2-naphthoyl chloride solution (300 mg/mL of CH$_2$Cl$_2$) was added. The reaction batch was stirred for 10 minutes at 75° C. The crude mixture was purified by preparative HPLC (Nucleosil 100, solvent: t-butylmethyl ether/hexane 1:2 with 1% methanol). The separation yielded 8 mg (29%) of epothilone E-21 naphthoylate.

$^1$H-NMR (400 MHz, CDCl$_3$); δ=6.64 (s, 17-H), 7.19 (s, 19-H), 5.67 (s, 21-H$_2$), 8.09 (dd, 3'-H), 7.96 (d, 4'-H), 7.89

(dd, 5'-H), 7.89 (dd, 6'-H), 7.58 (m, 7'-H), 7.58 (m, 8'-H), 8.67 (s, 9'-H); HRMS (DCI): $C_{37}H_{45}NO_3S$: [M$^+$] calculated 663.2866, found 663.2877.

Example 10

Example: [1S-[1R*,3R*(E),7R*,10S*,11R*,12R*,16S*]]-7,11-Dihydroxy-3-[2-[2-[[(2-methoxyethoxy)acetyloxy] methyl]-1-methyl-4-thiazolyl]ethenyl]-8,8,10,12-tetramethyl-4,17-dioxabicyclo[14.1.0]heptadecane-5,9-dione (R=G$^1$=G$^2$=H, G$^3$=O, G$^4$=Z$^3$C=O, Z$^3$=3',6'-dioxahexyl in formula Ia)

2-(2-Methoxyethoxy) acetic acid, 100 μL (880 μmol), is dissolved in 1.6 mL of THF. Then, 137.6 μL (880.0 μmol) of 2,4,6-trichlorobenzoyl chloride and 135 μL (968 μmol) of triethylamine were added. The batch was stirred for 1 hour at room temperature during which a colorless precipitate developed. The reaction solution was centrifuged and 120 μL of the supernatant was added to a solution of 23 mg (45 μmol) of epothilone E in 400 μL of THF. Then, 8.4 mg (46 μmol) of dimethylaminopyridine was added and the mixture was stirred for 20 minutes at room temperature. The purification of the crude product was done through preparative HPLC (Nucleosil 100, solvent: t-butylmethyl ether/hexane 1:2+2% methanol). Thus, 14.7 mg (52%) of 21-(3',6'-dioxaheptanoyl)-epothilone E were isolated.

$^1$H-NMR (300 MHz, CDCl$_3$): δ=6.60 (bs, 17-H), 7.16 (S, 19-H), 5.42 (s, 21-H$_2$), 4.52 (s, 21-H$_2$), 3.74 (m, 3'-H$_2$), 3.58 (m, 4'-H$_2$), 3.37 (s, 5'-H$_3$); HRMS (DCI): $C_{31}H_{47}NO_{10}S$: [M+H$^+$] calculated 626.2999, found 626.2975.

An Example of the synthesis of 21-acylamino-epothilones 10 is given in the following Example 11.

Example 11

Example: [1S-[1R*,3R*(E),7R*,10S*,11R*,12R*,16S*]]-7,11-Dihydroxy-8,8,10,12-tetramethyl-3-(1-methyl-2-[2-[(N-propionylamino)methyl]-4-thiazolyl]ethenyl]-4,17-dioxabicyclo[14.1.0]heptadecane-5,9-dione (R=H, G$^1$=G$^2$=H, G$^3$=NZ$^1$, Z$^1$=H, G$^4$=Z$^2$C=O, Z$^2$=Et in formula Ia)

Triethylamine, 70 μL (500 μmol) was dissolved in 250 μL of absolute THF and then cooled to 0° C. with ice water. Then, 53 μL (400 μmol) of methyl chloroformate was added to this solution. After approximately 5 minutes, 25 μL (334 μmol) of propionic acid was added dropwise and the mixture stirred for another 10–15 minutes. The mixture was heated to room temperature and the precipitate was centrifuged off. Then, 47 μL of the supernatant was added to a solution of 13 mg (26 μmol) of 21-amino-epothilone A in 250 μL of absolute THF and 5.4 μL (39.0 μmol) of triethylamine. After 20 minutes, the crude batch was purified by preparative TLC (solvent: CH$_2$Cl$_2$/MeOH 90:10). Thus, 11.2 mg (76%) of 21-amino-epothilone A-propionamide was obtained.

$^1$H-NMR (300 MHz, CDCl$_3$): δ=6.57 (bs, 17-H), 7.07 (s, 19-H), 2.28 (q, 2'-H$_2$), 1.18 (3'-H$_3$), 6.29 (t, NH); HR-MS (EI): $C_{29}H_{44}N_2O_7S$: calculated 564.2869, found 564.2854.

The Synthesis of Epothilones IV and of 21-Acyloxyepothilones 6 is described in Examples 12 to 18 that follow.

Derivatives 6 are described in DE 199 07 588.3 and can be obtained in general from the multi-step approach from 2, while the following process corresponds to DE 199 30 111.5, both of which are incorporated herein as set forth at length.

Example 12

Example: [1S-[1R*,3R*(E),7R*,10S*,11R*,12R*,16S*]]-3-[2-(3-Acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide (Formulae IVa and IVb: R=H, G$^{11}$=CH$_3$)

102 mg (0.2 mmol) of compound 2 was dissolved in 2 mL acetic anhydride and heated for 5 min. to 75° C. Then, the reaction medium was concentrated at 30° C./1 mbar to a viscous oil and separated on silica gel Si 60 (solvent: hexane/methyl-tert-butylether/methanol 66:33:1); in addition to 65 mg (41%) 6 17 mg (11%) each of IVa and IVb were eluted.

IVa: colourless oil; DC:R$_f$=0.66 (dichloromethane/methanol 95:5); UV (MeOH): $\lambda_{max}(\epsilon)$=203 (13800), 267 (13200), 315 nm (5000); $[\alpha]_D^{21}$=185.1 (c=0.94 in CHCl$_3$/MeOH 1:1); IR (KBr): ν=3446, 2965, 2936, 2877, 1742, 1691 cm$^{-1}$; $^1$H-NMR (CDCl$_3$): δ=2.43 (dd, J=14,8, 3.7 H-2a); 2.53 (dd, 14.8, 10.2, H-2b); 4.13 (m, 3-H); 3.33 (d, J=6.4, 3-OH); 1.86 (dt, J=15,0, 7.8, 14-Ha); 2.08 (m, 14-Hb); 5.39 (dd, J=7.8, 2.2, 15-H); 6.23 (sbr, 17-H); 6.95 (s, 19-H); 5.18 (s, 21-Ha); 5.71 (sbr, 21-Hb); 2.26 (Sbr, 27-H$_3$); 2.12 (s, CH$_3$CO); $^{13}$C-NMR (CDCl$_3$): δ=73.4 (C-3); 52.8 (C-4); 151.5 (C-16); 116.0 (C-17); 158.0 (C-18); 88.7 (C-19); 166.9 (C-20); 107.2 (C-21); 20.7 (C-22); 170.2, 21.2 (acetyl); HPLC/ESI-MS (acetonitrile/0.02 M ammonium acetate buffer pH 7, pos. ions): m/z 569 [M+NH$_4^+$].

IVb: colourless oil; DC : R$_f$=0.69 (conditions as above); $[\alpha]_D^{21}$=119.6 (c=1.1; CHCl$_3$/MeOH 1:1); $^1$H-NMR (CDCl$_3$):1.90 (m, 14-Ha); 2.09 (m, 14-Hb); 5.42 (dd, J=7.8, 2,2, 15-H); 6.92 (s, 19-H); 2.23 (s, 27-H$_3$); 2.10 (s, CH$_3$CO); $^{13}$C-NMR (CDCl$_3$): 150.8 (C-16); 116.5 (C-17); 17.2 (C-27); 170.3, 21.0 (acetyl);

Example 13

Example: [1S-[1R*,3R*(E),7R*,10S*,11R*,12R*,16S*]]-7,11-Dihydroxy-3-[2-[2-(methoxymethyl)-4-thiazolyl]-1-methylethenyl]-8,8,10,12-tetramethyl-4,17-dioxabicyclo [14.1.0]heptadecane-5,9-dione (6a, R=H, Nu=OCH$_3$)

14 mg (25 μmol) IVa or IVb (R=from example 12 above were heated in 1 mL methanol for 30 min. to 75° C., concentrated under vacuum and separated by preparative HPLC (RP-18, CH$_3$CN/H$_2$O1:1).

Yield 2.5 mg (19%). R$_f$(CH$_2$Cl$_2$/MeOH):0.33; $^1$H-NMR (CDCl$_3$): δ=4.71 (s, 21-CH$_2$); 3.49 (s, 21-OCH$_3$); $^{13}$C-NMR (CDCl$_3$): δ=59.1 (OCH$_3$); 71.5 (C-21); 167.8 (C-20); DCI-MS (i-butane:$^m/_z$=524.2609 [m+H$^+$], for $C_{27}H_{41}NO_7S$ calc. 524.2604.

Example 14

[1S-[1R*,3R*(E),7R*,10S*,11R*,12R*,16S*]]-7,11-Dihydroxy-8,8,10,12,16-pentamethyl-3-[1-methyl-2-[2-(phenoxymethyl)-4-thiazolyl]ethenyl]-4,17-dioxabicyclo [14.1.0]heptadecane-5,9-dione.

6,6 mg (11,7 μmol) of N-acetyl-21-methylene-epothilone A N-oxide was dissolved in 1,5 mL of dichloromethane and treated with 11.1 mg (120 μmol) of phenol dissolved in 300 μl of dichloromethane. After stirring the mixture at 75° C. for two hours the solvents were evaporated and the crude product purified by preparative TLC (solvent: CH$_2$Cl$_2$/methanol 95:5) to give 1,8 mg (30%) of 21-phenoxy-epothilone B.

$^1$H-NMR(400 MHz, CDCl$_3$): delta=6.59 (bs, 17-H), 6.99 (s, 19-H), 4.21 (s, 21-H$_2$), 6.78 und 7.16 (d, d, aromat. H); HR-MS (DCI): $C_{28}H_{43}NO_7S$, [M+H$^+$] calc. 538.2839, found 538.2832.

Example 15

Example: [1S-[1R*,3R*(E),7R*,10S*,11R*,12R*,16S*]]-3-[2-[2-[(Ethylthio)methyl]-4-thiazolyl)-1-methylethenyl]-7,11-dihydroxy-8,8,10,12,16-pentamethyl-4,17-dioxabicyclo[14.1.0]heptadecane-5,9-dione (8, R=CH$_3$, R$^1$=C$_2$H$_5$)

20 mg of compound 2 (R=CH$_3$) was transformed with acetic anhydride into a mixture of 6 (R$^1$=acetyl)and IVa and IVb from example 12 above and concentrated under vacuum to an oil. This oil was dissolved in 100 μl ethylmercaptane and heated for 1 hour to 105° C. Further, the mixture was brought to dryness under vacuum and the dried residue was separated by preparative DC (silica gel, petroleum ether/ethylacetate 1:1). Yield 5 mg (25 %)

$R_f$(petrolether/ethylacetate 1:1): 0.48; $^1$H-NMR (CDCl$_3$): δ=3.98 (s, 21-CH$_2$); 1.24, 2.60 (t, q, 21-SC$_2$H$_5$) (s, 21-OCH$_3$); DCI-MS (i-butane): $^m/_z$=554.

Example 16
[1S-[1R*,3R*(E),7R*,10S*,11R*,12R*,16S*]]-3-[2-[2-(Ethoxymethyl)-4-thiazolyl]-1-methylethenyl]-7,11-dihydroxy-8,8,10,12-tetramethyl-4,17-dioxabicyclo[14.1.0]heptadecane-5,9-dione 10 mg (19,7 μmol) of epothilone E were dissolved in a mixture of 100 μl of dichloromethane and 300 μl of diethylether and treated with 54,6 mg (236 μmol) of silver(I)-oxide and 47,6 μl (590 μmol) of iodoethane. After stirring over night at room temperature the mixture was filtered through Celite and evaporated to dryness. Purification of the crude product was achieved by preparative TLC (solvent: CH$_2$Cl$_2$/methanol 95:5) to give 8,8 mg (83,4%) of 21-ethoxy-epothilone A.

$^1$H-NMR (400 MHz, CDCl$_3$): delta=6.60 (br, 17-H), 7.11 (s, 19-H), 4.75 (s, 21-H$_2$), 3.65 (q, 1'-H$_2$), 1.27 (t, 2'-H$_3$); HR-MS (DCI): C$_{28}$H$_{43}$NO$_7$S, [M+H$^+$] calc. 538.2839, found 538.2832.

Example 17
[1S-[1R*,3R*(E),7R*,10S*,11R*,12R*,16S*]]-7,11-Dihydroxy-8,8,10,12-tetramethyl-3-[1-methyl-2-[2-[(2,3,4,6-tetraacetyl-alpha-glucosyloxy)methyl]-4-thiazolyl]ethenyl]-4,17-dioxabicyclo[14.1.0]heptadecane-5,9-dione
[1S-[1R*,3R*(E),7R*,10S*,11R*,12R*,16S*]]-7,11-Dihydroxy-8,8,10,12-tetramethyl-3-[1-methyl-2-[2-[(2',3',4',6'-tetraacetyl-beta-glucosyloxy)methyl]-4-thiazolyl]ethenyl]-4,17-dioxabicyclo[14.1.0]heptadecane-5,9-dione

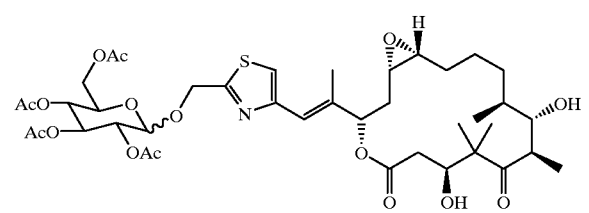

Epothilone E (50 mg, 98 μmol) and tetramethylurea (46 μl, 383 μmol) dissolved in 200 mL of dry CH$_2$Cl$_2$, were added to a suspension of silver trifluoromethanesulfonate (101 m, 393 μmol) and powdered molecular sieve 4 Å (500 mg) in 2 mL dry CH$_2$Cl$_2$. The mixture was stirred under N$_2$ atmosphere for 1 hour at room temperature. β-D-acetobromoglucose (121 mg, 295 μmol) dissolved in 200 μl dry CH$_2$Cl$_2$ was added. The reaction mixture was stirred at room temperature over night, filtered through Celite and concentrated. Purification by reversed phase chromatography (CH$_3$CN/H$_2$O 48:52) and subsequently silica gel (CH$_2$Cl$_2$/methanol 95:5) furnished alpha-glucoside (4.2 mg, 5%) and β-glucoside (5.6 mg, 6%) as colorless solids.

alpha-glucoside:
$^1$H-NMR (300 MHz, CDCl$_3$): delta=6.58 (bs, 17-H), 7.11 (s, 19-H), 4.82 (s, 21-H$_2$), 5.74 (d, 1'-H), 4.38 (ddd, 2'-H), 5.19 (t, 3'-H), 4.90 (dd, 4'-H), 3.94 (dt, 5'-H), 4.20 (m, 6'-H$_2$); DCI-MS (120 eV, NH$_4^+$): 857 [M+NH$_4^+$].

beta-glucoside:
$^1$H-NMR (400 MHz, CDCl$_3$): delta=6.59 (bs, 17-H), 7.14 (s, 19-H), 4.92 (d, 21-Ha), 5.06 (d, 21-Hb), 4.69 (d, 1'-H), 5.08 (t, 2'-H), 5.20 (t, 3'-H), 5.11 (t, 4'-H), 3.71 (m, 5'-H), 4.13 (dd, 6'-Ha), 4.25 (dd, 6'-Hb); DCI-MS (120 eV, NH$_4^+$): 857 [M+NH$_4^+$].

Example 18
[1S-[1R*,3R*(E),7R*,10S*,11R*,12R*,16S*]]-7,11-Dihydroxy-8,8,10,12-tetramethyl-3-[1-methyl-2-[2-[(6'-acetyl-alpha-glucosyloxy)methyl]-4-thiazolyl]ethenyl]-4,17-dioxabicyclo[14.1.0]heptadecane-5,9-dione The β-glucoside obtained above (4.8 mg, 5,8 μmol) was dissolved in 50 μl DMSO. Phosphate-buffer (4 ml, 20 mM, pH=7) was added and the reaction mixture was sonicated for 5 minutes. Pig liver esterase (0,3 ml, Boehringer Mannheim) was added and stirring was continued for additional 3 hours. The mixture was extracted with ethylacetate and the combined organic extracts were concentrated. Purification by reversed phase chromatography (CH$_3$CN/H$_2$O 38:62) gave 1 mg (24%) of the glucoside.

$^1$H-NMR (600 MHz, CDCl$_3$): delta=6.62 (bs, 17-H), 7.15 (s, 19-H), 4.95 (d, 21-Ha), 5.14 (d, 21-Hb), 4.53 (d, 1'-H), 3.45 (dd, 2'-H), 3.57 (t, 31-H), 3.42 (t, 4'-H), 3.50 (m, 5'-H), 4.30 (dd, 6'-Ha), 4.48 (dd, 6'-Hb), 2.12 (s, acetyl-H$_3$).

The synthesis of 21-sulfonyloxy-epothilones 6 is given in Examples 19 and 20 that follow.

Example 19
Example: [1S-[1R*,3R*(E),7R*,10S*,11R*,12R*,16S*]]-7,11-Dihydroxy-8,8,10,12,16-pentamethyl-3-[1-methyl-2-[2-[(p-toluenesulfonyloxy)methyl]-4-thiazolyl]ethenyl]-4,17-dioxabicyclo [14.1. 0]heptadecane-5,9-dione (R=Me, G$^1$=G$^2$=H, G$^3$=O, G$^4$=Z$^4$SO$_2$, Z$^4$=p-toluoyl in formula Ia)

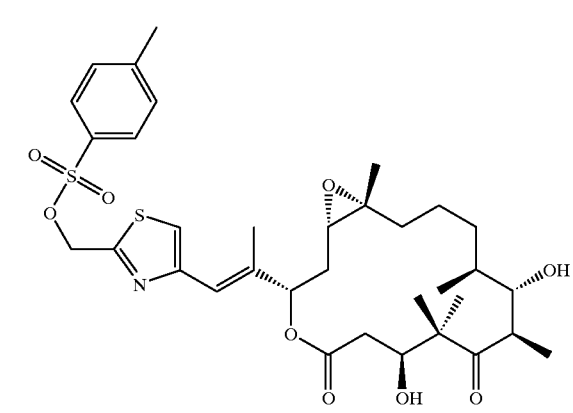

To a stirred solution of 104 mg epothilone F (199 μmol, 1 equivalent) in 5 mL CH$_2$Cl$_2$ at 0° C. under Argon was added 0.17 mL N,N-diisopropylethylamine (993 μmol, 5 equivalents) followed by 45 mg of p-toluenesulfonyl chloride (238 μmol, 1.2 equivalents). The mixture was stirred at 25° C. for 47 hours to allow complete consumption of starting material. The reaction was poured into 40 mL saturated aqueous NaHCO$_3$. The aqueous layer was extracted with CH$_2$Cl$_2$ (3×50 mL). The combined organic layers were dried over Na$_2$SO$_4$ and concentrated under vacuum. The crude material was chromatographed using 50% ethyl acetate in hexanes to yield 18 mg (16%) of the 21-chloro-epothilone B and 85 mg (63%) of 21-tosyloxy-epothilone B, as a clear oil. MS (ESI$^+$): 678.4 (M+H)$^+$.

A reaction of epothilone A with p-toluenesulfonylchloride in an analogous manner led to the formation of 21-tosyloxyepothilone A. A reaction of epothilone A-N-oxide with p-toluenesulfonylchloride led to the formation of a mixture of 21-tosyloxy-epothilone A and 21-chloro-epothilone A which were separeted by chromatography.

21-Tosyloxy-epothilone A:

$^1$H-NMR (300 MHz, CDCl$_3$): δ=6.54 (bs, 17-H), 7.15 (s, 19-H), 5.29 (s, 21-H$_2$), 7.82 (d, 2',6'-H), 7.34 (dm, 3†,5-H), 2.44 (s, 7'-H$_3$).

21-Chloro-epothilone A:

$^1$H-NMR (300 MHz, CDCl$_3$): δ=6.59 (bs, 17-H), 7.16 (s, 19-H), 4.81 (s, 21-H$_2$), HRMS (DCI): C$_{26}$H$_{38}$NO$_6$S: [M+H$^+$] calculated 528.2187, found 528,2154.

Example 20

[1S-[1R*,3R*(E),7R*,10S*,11R*,12R*,16S*]]-3-[2-[2-(Bromomethyl)-4-thiazolyl]-1-methylethenyl]-7,11-dihydroxy-8,8,10,12-tetramethyl-4,17-dioxabicyclo[14.1.0]heptadecane-5,9-dione

[1S-[1R*,3R*(E),7R*,10S*,11R*,12R*,16S*]]-3-[2-(5-Bromo-2-methyl-4-thiazolyl)-1-methylethenyl]-7,11-dihydroxy-8,8,10,12-tetramethyl-4,17-dioxabicyclo[14.1.0]heptadecane-5,9-dione 45 mg (91 μmol) of epothilone A was dissolved in 8 mL absolute THF in an atmosphere of N$_2$ and cooled to minus 90° C. 61 μl (406 μmol) of tetramethylethylendiamine and 270 μl (406 μmol) of t-butyllithium in hexane were added. After ten minutes of stirring at minus 90° C., 21 μl (406 μmol) of bromine was added. After 5 minutes of stirring the reaction was quenched with 10 mL saturated ammonium-chloride solution at minus 90° C. The mixture was warmed to room temperature with continued stirring and extracted with ethylacetate. The organic layer was dried with sodium sulfate and evaporated to dryness. Separation by preparative HPLC gave 2.6 mg (5%) of 21-bromo-epothilone A and 2.1 mg (4.0%) of 19-bromo-epothilone A.

$^1$H-NMR (600 MHz, CDCl$_3$): delta=6.58 (s, 17-H), 7.17 (s, 19-H), 4.70 (s, 21-H$_2$); HR-MS (DCI): C$_{26}$H$_{38}$NO$_6$SBr, [M+NH$_4^+$] calc. 589.1916 $^{79}$Br, found 591.1903 $^{81}$Br.

Example 21

[1S-[1R*,3R*(E),7R*,10S*,11R*,12R*,16S*]]-3-[2-[2-(Cyanomethyl)-4-thiazolyl]-1-methylethenyl]-7,11-dihydroxy-8,8,10,12,16-pentamethyl-4,17-dioxabicyclo[14.1.0]heptadecane-5,9-dione

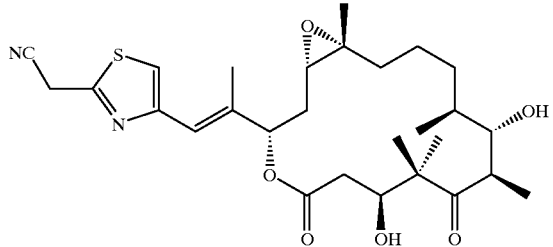

(i) By means of a Katada reaction epothilone B-N oxide was rearranged to epothilone F. To a stirred solution of 104 mg epothilone F (199 μmol 5, equivalents) in 5.0 mL CH$_2$CH$_2$ at 0° C. under Argon was added 0.17 mL n,n-diisopropyl-ethyl amine (0.993 mmol, 5 equivalents) followed by the addition of 0.045 g of p-toluenesulfonyl chloride (238 μmol, 1.2 equivalents). The mixture was stirred at 25° C. for 47 hours to allow complete consumption of starting material (SM). The mixture was then poured into 40 mL saturated aqueous NaHCO$_3$. The aqueous layer was extracted with CH$_2$Cl$_2$ (3×50 mL). The combined organic layers were dried over Na$_2$SO$_4$ and concentrated under vacuum. The crude material was then chromatographed using 50% ethyl acetate in hexanes to yield 18 mg of the C21 chloride (16%) and 85 mg of the desired tosylate (63%) as a clear oil.

(ii) To a stirred solution of 84 mg SM from above (124 μmol, 1 equivalent) in 3.50 mL CH$_2$Cl$_2$ under Argon at 25° C. was added 40 mg KCN (620 μmol, 5 equivalents) and 33 mg 18-crown-6 (124 μmol, 1 equivalent). The mixture was allowed to stir at 25° C. for 15 hours, at which time the starting material was completely consumed. The mixture was then directly loaded onto a silica gel column and chromatographed using 2:1 ethyl acetate:hexanes as an eluent to afford 41 mg of the desired nitrile (61%) as a colorless solid.

Example 22

[4S-[4R*,7S*,8R*,9R*,15R*(E)]]-16-[2-[2-(Cyanomethyl)-4-thiazolyl]-1-methylethenyl]-4,8-dihydroxy-5,5,7,9,13-pentamethyl-1-oxa-13(Z)-cyclohexadecene-2,6-dione

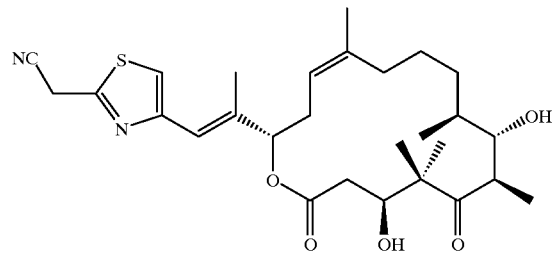

Anhydrous tetrahydrofuran (5.0 mL) was placed in an oven-dried flask under Argon and cooled to −78° C. Under Argon flow, WCl$_6$ (300 mg, 0.756 mmol, 2 equivalents) was added to the cold tetrahydrofuran followed by n-butyllithium (0.946 mL of 1.6 M solution in hexanes, 1.51 mmol, 4 equivalents). The reaction flask was removed from the −78° C. cooling bath and stirred at ambient temperature for 15 minutes. The reaction was then placed into a 0° C. bath and stirred for an additional 5 minutes. In a separate flask, 21-cyano-epothilone B (72 mg, 0.135 mmol) previously azeotroped overnight from toluene in vacuo to dry was cooled in ice to 0° C. and the bright green tungsten reagent solution (2.12 mL) was added. The reaction was maintained at 0° C. for 20 minutes. TLC showed the disappearance of starting material. The reaction was quenched with saturated aqueous NaHCO$_3$ (10 mL) and partitioned between saturated aqueous NaHCO$_3$ (20 mL) and ethyl acetate (50 mL). The aqueous phase was extracted three times with ethyl acetate. The combined organic layers were washed with water (25 mL) and brine (15 mL) and then dried over Na$_2$SO$_4$ before concentration in vacuo. The crude material was purified by chromatography on silica gel with 40% ethyl acetate in hexanes to obtain 43 mg (61%) of 21-cyano-epothilone D. MS (ESI$^+$): 516.3 (M+H)$^+$.

Example 23

[1S-[1R*,3R*(E),7R*,10S*,11R*,12R*,16S*]]-7,11-Dihydroxy-3-[2-[2-(1H-imidazol-1-ylmethyl)-4-thiazolyl]-1-methylethenyl]-8,8,10,12,16-pentamethyl-4,17-dioxabicyclo[14.1.0]heptadecane-5,9-dione

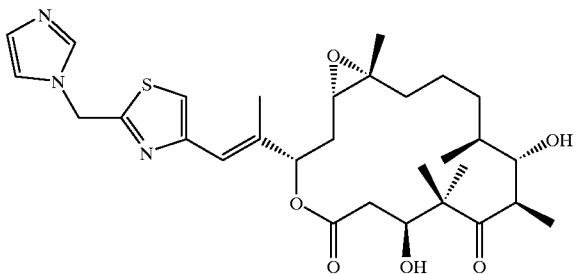

To a stirred solution of 6 mg 21-tosyloxy-epothilone B (8.9 μmol, 1 equivalents) in 1.0 mL dimethylformamide under Argon was added imidazole (4.8 mg, 71 μmol, 8 equivalents) and $K_2CO_3$ (12.3 mg, 0.0890 mmol, 10 equivalents). The mixture was allowed to stir at 25° C. for 5 hours. The solvent was removed in vacuo, and the reaction mixture was chromatographed on silica gel using 1% $Et_3N$, 3% MeOH in $CHCl_3$ as eluent to afford 1.4 mg (27%) of 21-imidazoline-epothilone B, as a clear oil. MS ($ESI^+$): 574.4 $(M+H)^+$.

An example of the synthesis of Epothilone-20-carbaldehydes 13 are given in the following Examples 24 and 25.

Example 24

Example: [1S-[1R*,3R*(E),7R*,10S*,11R*,12R*,16S*]]-3-[2-(2-Formyl-4-thiazolyl)-1-methylethenyl]-7,11-dihydroxy-8,8,10,12-tetramethyl-4,17-dioxabicyclo[14.1.0] heptadecane-5,9-dione ($G^6$=H, $G^9$=O in formula IIb)

Epothilone E, 58 mg (114 μmol), was dissolved in 1 mL of $CH_2Cl_2$. At intervals of 10 minutes, 295 mg (3.4 mmol) of manganese dioxide was added three times and the mixture stirred at room temperature. After 40 minutes, the manganese dioxide was filtered off and washed with methanol. The combined organic phases were evaporated to dryness and the crude product was purified using preparative HPLC (Nucleosil 100, solvent: t-butylmethyl ether/hexane with 3% methanol). Thus, 36 mg (62%) of epothilone A-20-carbaldehyde were obtained.

$^1$H-NMR (400 MHz, $CDCl_3$): delta=6.67 (S, 17-H), 7.53 (S, 19-H), 9.98 (d, 21-H); HRMS (DCI): $C_{26}H_{37}NO_7S$: $[M+H^+]$ calculated 508.2369, found 508.2367.

Example 25

[1S-[1R*,3R*(E),7R*,10S*,11R*,12R*,16S*]]-3-[2-(2-Formyl-4-thiazolyl)-1-methylethenyl]-7,11-dihydroxy-8,8,10,12,16-pentamethyl-4,17-dioxabicyclo[14.1.0]heptadecane-5,9-dione

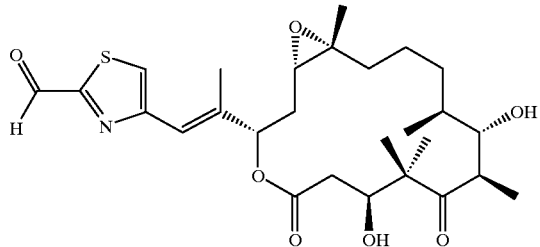

Epothilone F (180 mg, 344 μmol, 1 equivalents) was dissolved in $CH_2Cl_2$ under Argon. Manganese dioxide (900 mg, 10.3 mmol, 30 equivalents) was added, and the reaction was stirred at 25° C. for 2 hours. Additional manganese dioxide (400 mg, 4.60 mmol, 13.4 equivalents) was added and the reaction was stirred for 2 hours more. The mixture was filtered through Celite, rinsed with $CH_2Cl_2$, and then concentrated in vacuo. The crude material was chromatographed on silica gel eluting with 50% ethyl acetate in hexanes to provide 92 mg (51%) of 21-formyl-epothilone B as a colorless solid. ESI-MS: 522.3 $(M+H)^+$.

The synthesis of 21-alkylidene epothilones 15 is given in Example 26 which follows.

Example 26

Example: [1S-[1R*,3R*(E),7R*,10S*,11R*,12R*,16S*]]-3-[2-(2-Ethenyl-4-thiazolyl)-1-methylethenyl]-7,11-dihydroxy-8,8,10,12-tetramethyl-4,17-dioxabicyclo[14.1.0] heptadecane-5,9-dione (R=H, $G^6=G^8=Z^7$=H, $G^7=CZ^7$ in formula IIa)

Methyl instand-ylid (Fluka), 50 mg, was treated with 17 mg of methylphosphonium bromide and suspended in 500 μL absolute THF. The batch was placed in an ultrasound bath for 2–3 minutes and then stirred at room temperature. When the reaction solution had developed a bright yellow color, the suspension was added dropwise to a solution of 15.2 mg (30 μmol) A-aldehyde in 100 μL of absolute THF. After 1 hour, the batch was diluted with water and extracted three times with dichloromethane. The organic phase was evaporated and dried in high vacuum. Separation of the crude mixture was done through preparative HPLC (Nucleosil 100, solvent: t-butylmethyl ether/hexane 1:2+1% methanol). Thus, 1.7 mg (11%) of 20-vinyl-epothilone A was isolated.

$^1$H-NMR (400 MHz, $CDCl_3$): δ=6.59 (bs, 17-H), (7.04) (s, 19-H), 6.86 (dd, 21-H), 6.05 (d, 1'-Hb), 5.55 (d, 1'-Ha); HRMS (DCI): $C_{27}H_{39}NO_6S$: $[M+H^+]$ calculated 506.2576, found 506.2589.

The synthesis of 21-Imino-epothilones 22 is given in the following Example.

Example 27

Example: [1S-[1R*,3R*(E),7R*,10S*,11R*,12R*,16S*]]-7,11-Dihydroxy-3-[2-[2-(methoxyimino)-4-thiazolyl]-1-methylethenyl]-8,8,10,12-tetramethyl-4,17-dioxabicyclo [14.1.0]heptadecane-5,9-dione (R=$G^6$=H, $G^7$=N, $G^8=OZ^{10}$, $Z^{10}$=Me in formula IIa)

Pyridine, 10 μL (124 μmol), and 113 μL (54 μmol) of o-methylhydroxyammonium chloride solution (40 mg/mL) was added to a solution of 25 mg (49 μmol) epothilone A-21-aldehyde in 200 μL of methanol. After stirring the reaction batch for 1 hour at room temperature, the solvent was removed and the residue taken up in ethyl acetate. The organic phase was extracted once with water and dried with $Na_2SO_4$. The purification of the crude product was done with the aid of preparative HPLC (Nucleosil 100, solvent: t-butylmethyl ether/hexane 1:2 with 1% methanol). Thus, 9 mg (36%) (21E)- and 7 mg (27%) of (21Z)-21-(N-Methoxyimino)-epothilone A were obtained.

(21E)-isomer $^1$H-NMR (300 MHz, $CDCl_3$): δ=6.61 (bs, 17-H), 7.12 (s, 19-H), 8.22 (s, 21-H), 4.01 (s, 1'-$H_3$), (21Z)-isomer $^1$H-NMR (300 MHz, $CDCl_3$): δ=6.65 (bs, 17-H), 7.36 (bs, 19-H), 7.86 (d, 21-H), 4.15 (s, 1'-$H_3$). HRMS (DCI): $C_{27}H_{40}N_2O_7S$: $[M+H^+]$ calculated 537.2634, found 537.2637.

Example 28

[1S-[1R*,3R*(E),7R*,10S*,11R*,12R*,16S*]]-7,11-Dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione Epothilone A-21-aldehyde (19 mg, 38 μmol) was dissolved in 1 mL dry $CH_2Cl_2$. Powdered molecular sieves 4

Å and benzylamine (4.5 mg, 41 µmol) was added. The reaction mixture was stirred at room temperature for 45 minutes, filtered through Celite and concentrated. Purification on silica gel (CH$_2$Cl$_2$/methanol 95:5) gave 21-benzylimino-epothilone A (10 mg, 45%).

$^1$H-NMR (300 MHz, CDCl$_3$): delta=6.62 (bs, 17-H), 7.21 (s, 19-H), 8.46 (s, 21-H), 4.87 (d, 1'-H$_2$).

Example 29

Example: [1S-[1R*,3R*(E),7R*,10S*,11R*,12R*,16S*]]-3-[2-(2-Acetyl-4-thiazolyl)-1-methylethenyl]-7,11-dihydroxy-8,8,10,12-tetramethyl-4,17-dioxabicyclo[14.1.0]heptadecane-5,9-dione (G$^6$=Me, G$^9$=O in formula IIb) and 20-(21,22-epoxyethyl)-epothilone A (G$^1$=H, G$^2$,G$^5$=CH$_2$—O in formula Ib)

Epothilone A-21-aldehyde (Example 28), 10 mg (20 µmol), was dissolved in 200 µL CH$_2$Cl$_2$, an excess of diazomethane in ether was added and the mixture was stirred at room temperature. After 15 minutes, the reaction batch was evaporated and separated using preparative TLC (silica gel 60, solvent: CH$_2$Cl$_2$/methanol 95:5). Thus, 4.5 mg (44%) 21-acetyl-epothilone A and 1.9 mg (19%) 20-epoxyethyl-epothilone A were obtained.

[1S-[1R*,3R*(E),7R*,10S*,11R*,12R*,16S*]]-3-[2-(2-Acetyl-4-thiazolyl)-1-methylethenyl]-7,11-dihydroxy-8,8,10,12-tetramethyl-4,17-dioxabicyclo[14.1.0]heptadecane-5,9-dione:

$^1$H-NMR (300 MHz, CDCl$_3$): δ=6.62 (bs, 17-H), 7.45 (s, 19-H), 2.71 (s, 1'-H$_3$).

[1S-[1R*,3R*(E),7R*,10S*,11R*,12R*,16S*]]-7,11-Dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione:

$^1$H-NMR (300 MHz, CDCl$_3$): δ=6.58 (bs, 17-H), 7.09 (s, 19-H), 4.22 (t, 21-H), 3.00 (m, 1-Ha), 3.23 (dd, 1'-Hb).

Example 30

[1S-[1R*,3R*(E),7R*,10S*,11R*,12R*,16S*]]-7,11-Dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione To 26 mg (49 µmol) of iodomethyltriphenylphosphonium iodide suspended in 1 mL of absolute THF, 49 µl (49 µmol) of a solution of sodium hexamethyldisilazan in THF was added. After stirring for one minute at room temperature the mixture was cooled to minus 78° C., 14 µl (80 µmol) of HMPA and then a solution of 20 mg (40 µmol) of epothilone A 21-aldehyde in 0.2 mL of absolute THF were added. At the same temperature the reaction mixture was stirred for 30 minutes and then quenched with 1 mL of saturated ammonium chloride solution. After warming to room temperature the reaction mixture was extracted with ethylacetate, the organic layer was separated, dried with sodium sulfate and evaporated to dryness. Separation was achieved by preparative HPLC to give 8,4 mg (34%) of the (20Z)-iodovinyl and 2 mg (8%) of the (20E)-iodovinyl analog.

E-Isomer
$^1$H-NMR (600 MHz, CDCl$_3$): delta=6.56 (s, 17-H), 7.07 (s, 19-H), 7.53 (d, 21-H), 7.39 (d, 1'-H);

Z-Isomer
$^1$H-NMR (300 MHz, CDCl$_3$): delta=6.63 (bs, 17-H), 7.21 (s, 19-H), 7.82 (dd, 21-H), 7.03 (d, 1'-H$_2$); HR-MS (DCI): C$_{27}$H$_{38}$NO$_6$SI, [M+H$^+$] calc. 632.1543, found 632.1593.

Example 31

[1S-[1R*,3R*(E),7R*,10S*,11R*,12R*,16S*]]-3-[2-(2-Ethynyl-4-thiazolyl)-1-methylethenyl]-7,11-dihydroxy-8,8,10,12-tetramethyl-4,17-dioxabicyclo[14.1.0]heptadecane-5,9-dione 18,5 µl (131 µmol) of diisopropylamine dissolved in 0.4 mL of absolute THF was treated at minus 10° C. with 70 µl (105 µmol) of n-buthyllithium in hexane. After one hour at 0° C. 17 mg (27 µmol) of (20Z)-iodovinyl derivative in 0,5 mL of absolute as THF was added to the solution. After one hour stirring at 0° C. the reaction was quenched with 2 mL saturated ammoniumchloride solution. The reaction mixture was extracted with ethylacetate, the organic phase evaporated to dryness and separated by preparative HPLC. Yield 2,4 mg (36%).

$^1$H-NMR (400 MHz, CDCl$_3$): delta=6.60 (bs, 17-H), 7.15 (s, 19-H), 3.46 (s, 21-H); HR-MS (DCI): C$_{27}$H$_{37}$NO$_6$S, [M+NH$_4^+$] calc. 521.2685, found 521.2696.

Examples of the synthesis of 21-alkylamino-epothilones 10 and 11 are given in Examples 32 to 36 that follow.

Example 32

[1S-[1R*,3R*(E),7R*,10S*,11R*,12R*,16S*]]-7,11-Dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione

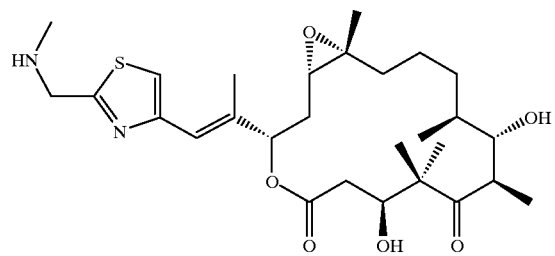

To a stirred solution of epothilone B-21-aldehyde (17 mg, 0.033 mmol) in 2.0 mL CH$_3$CN under Argon at 0° C. was added a 2.0 M solution of methylamine (0.16 mL, 0.326 mmol, 10 equivalents). After 15 min, 6 mg NaBH$_3$CN (0.098 mmol, 3 equivalents) was added and the mixture was allowed to stir at 0° C. for 30 minutes. Acetic acid was then added dropwise until the solution was approximately pH 7. After the mixture was stirred an additional 2 hours, 20 mL of 28% aqueous NH$_4$OH$_{(aq)}$ was added. The mixture was stirred for 5 minutes and then extracted with 75 mL ethyl acetate. The organic layer was dried over Na$_2$SO$_4$ and concentrated under vacuum. The crude material a was then chromatographed using silica gel eluted with 1% Et$_3$N, 2% MeOH in CHCl$_3$ to yield 8 mg (47%) of the 21-N-methylamino-epothilone B as a cloudy oil. MS (ESI$^+$): 537.4 (M+H)$^+$.

Example 33

[1S-[1R*,3R*(E),7R*,10S*,11R*,12R*,16S*]]-3-[2-[2-[[[2-(Dimethylamino)ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione

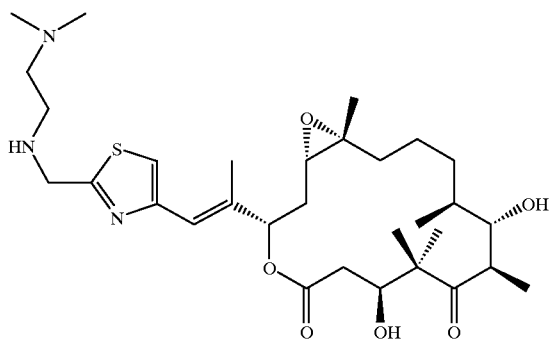

To a stirred solution of epothilone B-21-aldehyde (15 mg, 0.029 mmol) in 2.0 mL CH$_3$CN under Argon at 25° C. was added N,N-dimethylethylenediamine (31 µL, 0.288 mmol, 10 equivalents). After 10 min, 5 mg NaBH$_3$CN (0.086 mmol, 3 equivalents) was added and the mixture was allowed to stir at 25° C. for 30 min. AcOH was then added dropwise until the solution was approximately pH 7. After the mixture was stirred an additional 2 hours, 20 mL of 28% aqueous NH$_4$OH$_{(aq)}$ was added. The mixture was stirred for 5 minutes and then extracted with 75 mL ethyl acetate. The organic layer was dried over Na$_2$SO$_4$ and concentrated under vacuum. The crude material was then chromatographed using silica gel eluted with 1% Et$_3$N, 5% MeOH in CHCl$_3$ to yield 5.8 mg (34%) of the 21-(2-N,N-Dimethylaminoethyl)amino-epothilone B as a clear oil. MS (ESI$^+$): 594.5 (M+H)$^+$.

Example 34

[1S-[1R*,3R*(E),7R*,10S*,11R*,12R*,16S*]]-3-[2-(2-[(Dimethylamino)methyl]-4-thiazolyl]-1-methylethenyl]-7,11-dihydroxy-8,8,10,12,16-pentamethyl-4,17-dioxabicyclo[14.1.0]heptadecane-5,9-dione

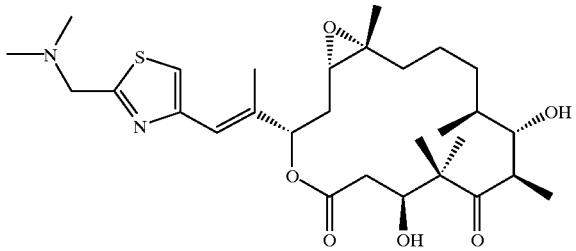

To a stirred solution of amine (19 mg, 0.0363 mmol) in 1.0 mL CH$_3$CN under Argon was added formaldehyde (0.04 mL of 37% aqueous solution, 0.1817 mmol, 5 equivalents) and 7 mg NaBH$_3$CN (0.1089 mmol, 3 equivalents). The mixture was allowed to stir 20 minutes. Acetic acid (1 drop) was added and the mixture was stirred an additional 40 minutes. The crude reaction mixture was applied directly to a silica gel column and eluted with 1% Et$_3$N, 1% MeOH in CHCl$_3$ to yield 2.5 mg (12%) of 21-N,N-dimethylamino-epothilone B. MS (ESI$^+$): 551.4 (M+H)$^+$.

Example 35

[1S-[1R*,3R*(E),7R*,10S*,11R*,12R*,16S*]]-3-[2-[2-[[Bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione

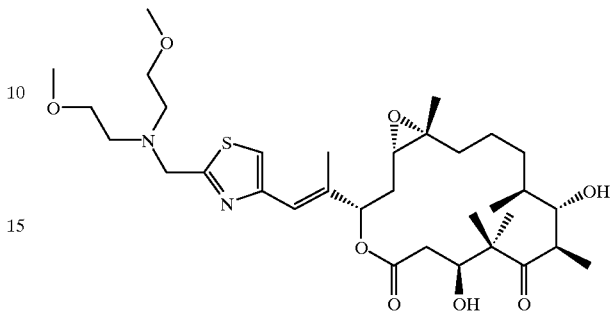

To a stirred solution of aldehyde (6.8 mg, 0.013 mmol) in 2.0 mL CH$_3$CN under Argon at 0° C. was added bis-(2-methoxyethyl)amine (19 µL, 0.130 mmol, 10 equivalents). After 15 minutes, 2.5 mg NaBH$_3$CN (0.039 mmol, 3 equivalents) was added and the mixture was allowed to stir at 0° C. for 30 minutes. Acetic acid was then added dropwise until the solution was approximately pH 7. After the mixture was stirred an additional 2 hours, 10 mL of 28% aqueous NH$_4$OH$_{(aq)}$ was added. The mixture was stirred for 5 minutes and then extracted with 75 mL ethyl acetate. The organic layer was dried over Na$_2$SO$_4$ and concentrated under vacuum. The crude material was then chromatographed using silica gel eluted with 1% Et$_3$N, 1% MeOH in CHCl$_3$ to yield 5.6 mg (67%) of the 21-(Bis-2-methoxyethyl)amino-epothilone B, as an oil. MS (ESI$^+$): 639.5 (M+H)$^+$.

Example 36

[1S-[1R*,3R*(E),7R*,10S*,11R*,12R*,16S*]]-7,11-Dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione

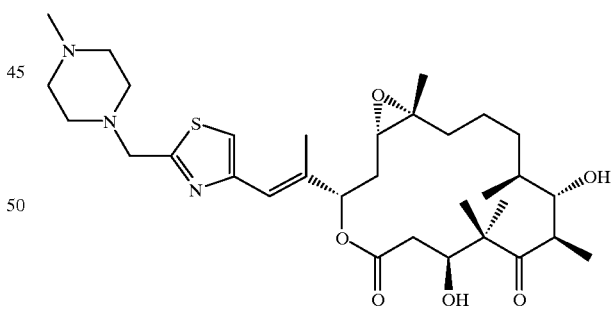

To a stirred solution of aldehyde (11 mg, 0.0211 mmol) in 1.0 mL CH$_3$CN under Argon was added 1-methylpiperazine (21 mg, 0.2109 mmol, 10 equivalents) and NaBH$_3$CN (4 mg, 0.0633 mmol, 3 equivalents). The mixture was allowed to stir 20 minutes. Acetic acid was then added dropwise until the solution was approximately pH 7. After the mixture stirred an additional 2 hours, 10 mL of 28% aqueous NH$_4$OH$_{(aq)}$ was added. The mixture was extracted with CH$_2$Cl$_2$ (2×75 mL). The organic layer was dried over Na$_2$SO$_4$ and concentrated under vacuum. The crude 2g material was then chromatographed using silica gel eluted with 1% Et$_3$N, 5% MeOH in CHCl$_3$ to yield 10.7 mg (84%)

of the 21-(N-methylpiperazine)amino -epothilone B, as a white foamy oil. MS (ESI+): 606.4 (M+H)+.

Example 37

Example: [1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid ($G^6$=$OZ^5$, $Z^5$=H, $G^9$=O in formula IIb)

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid methyl ester ($G^6$=$OZ^5$, $Z^5$=Me, $G^9$=O in formula IIb)

Epothilone A-21-aldehyde, 8.0 mg (16 μmol), was dissolved in 300 μL of a THF/water mixture (9:1) and 24.0 mg (194 μmol) silver(I) oxide was added. The reaction mixture was stirred for 12 hours at room temperature. Then the solvent was removed and the residue was taken up in ethyl acetate. Evaporation of the solvent gave the unstable carboxylic acid which was characterised by HPLC/ESI-MS: $t_r$=13.8 min; $m/z$=522 (M–H)− (RP-18 silica gel, $CH_3CN$ (10 mM $NH_4OAc$ buffer gradient 10:90 to 45:55). Preferably the organic phase was not evaporated but washed twice with 0.1% hydrochloric acid and once with water and then treated with an excess of diazomethane. The mixture was stirred for 10 minutes at room temperature. After removal of the solvent, the crude product was purified by preparative HPLC (Nucleosil 100, solvent: t-butylmethyl ether/hexane 1:2 with 1% methanol), whereupon 2.5 mg (30%) of epothilone A-21-carboxylic acid methyl ester were obtained.

$^1$H-NMR (400 MHz, $CDCl_3$): δ=6.73 (bs, 17-H), 7.42 (s, 19-H), 4.00 (s, 1'-$H_3$), HRMS (DCI): $C_{27}H_{39}NO_8S$: [M +H+] calculated 537.2396, found 537,2408.

Example 38

Biological Characterization of Epothilone Derivatives

Cytostatic Activity

Epothilone derivatives inhibit the growth of mammal cell cultures, and also of cell lines which are resistant to other cyclostatics.

Growth Inhibition of Transformed Cells of Mouse and Human Carcinoma and Leukemia Cell Lines Growth inhibition of the following cell lines was measured in microtiter plates: L929 (DSM ACC 2), mouse connective tissue fibroblasts; KB-3.1 (DSM ACC 158), human cervix carcinoma; KB-V1 (DSM ACC 149), human cervix carcinoma, multidrug-resistant; PC-3 (ATCC CRL 1435), human prostate adenocarcinoma; SK-OV-3 (ATCC HTB-77), human ovary adenocarcinoma; A-549 (DSM ACC 107), human lung carcinoma; K-562 (ATCC CCL-243), human chronic myelogenous leukemia; U-937 (DSM ACC 5), human histiocytic lymphoma. The cell lines were obtained from DSM (German Collection of Microorganisms und Cell Cultures), Braunschweig, Germany, or ATCC (American Type Culture Collection), Rockville, Md., U.S.A. Aliquots of suspended cells(50000/ml) were given to a serial dilution of the inhibitor. As a parameter of growth, we measured the reduction of MTT 3-[4,5-dimethylthiazol-2-yl]-2,5-diphenyltetrazolium bromide) or, in the case of leukemia cells, that of WST-1 (Boehringer Mannheim, Germany) after an incubation period of 5 days. The resulting values were related to control cells, to which only the solvent methanol had been added. These values were set to 100%. The IC50 (concentration that caused a growth reduction of 50%) were derived from inhibition curves (percentage of MTT reduction in dependence of inhibitor concentration).

| | $IC_{50}$ [ng/mL] | | | | | | |
|---|---|---|---|---|---|---|---|
| Compound | L929 mouse | KB-3.1 cervix | KB-V1* cervix | PC-3 prostate | SK-OV-3 ovary | A-549 lung | K-562/U-937 leukemia |
| 21-chloro-epo A [3] | 170 | 60 | 8 | | | 10 | 12 (K-562) |
| epo A-20-carb-aldoxime [22a] | 7 | | | | | | |
| epo A-20-carb-aldehyde hydrazone | 12 | | | | | | |
| 21-azido-epo A [22b] | 6 | | | | | | |
| 21-amino-epo A [9] | 8 | 4 | 30 | 3 | 4 | | 3 (U-937) |
| 20-vinyl-epo A [15] | 3 | 3 | 3 | 0.4 | 1 | | 1.5 (U-937) |
| 21-azido-epo B [7] | 0.6 | 0.5 | 0.5 | 0.4 | | | |
| 21-amino-epo B [9] | 0.5 | 0.4 | 1.5 | 1.5 | | | |

*Multiresistant cell line

We claim:
1. Compound having the general formula I

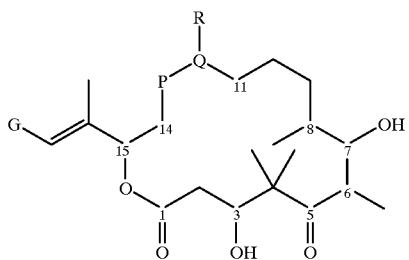

where:
P—Q is a C, C double bond or an epoxide;
G is

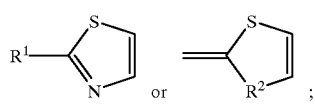

R is selected from the group of H, alkyl, and substituted alkyl;
$R^1$ is selected from the group consisting of

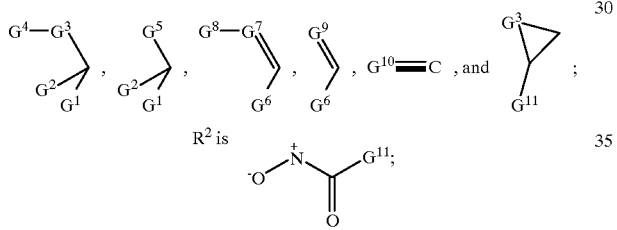

$R^2$ is

$G^1$ is selected from the group of H, halogen, CN, alkyl and substituted alkyl;
$G^2$ is selected from the group of H, alkyl, and substituted alkyl;
$G^3$ is selected from the group of O, S, and $NZ^1$;
$G^4$ is selected from the group of H, alkyl, substituted alkyl, $OZ^2$, $NZ^2Z^3$, $Z^2C=O$, $Z^4SO_2$, and optionally substituted glycosyl;
$G^5$ is selected from the group of halogen, $N_3$, NCS, SH, CN, NC, $N(Z^1)_3^+$ and heteroaryl;
$G^6$ is selected from the group of H, alkyl, substituted alkyl, $CF_3$, $OZ^5$, $SZ^5$, and $NZ^5Z^6$;
$G^7$ is $CZ^7$ or N;
$G^8$ is selected from the group of H, halogen, alkyl, substituted alkyl, $OZ^{10}$, $SZ^{10}$, $NZ^{10}Z^{11}$;
$G^9$ is selected from the group of O, S, —NH—NH— and —N=N—;
$G^{10}$ is N or $CZ^{12}$;
$G^{11}$ is selected from the group of $H_2N$, substituted $H_2N$, alkyl, substituted alkyl, aryl, and substituted aryl;
$Z^1$, $Z^6$, $Z^9$, and $Z^{11}$ are independently selected from the group H, alkyl, substituted alkyl, acyl, and substituted acyl;
$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;
$Z^4$ is selected from the group of alkyl, substituted alkyl, aryl, substituted aryl, and heterocycle;
$Z^7$ is selected from the group of H, halogen, alkyl, substituted alkyl, aryl, substituted aryl, $OZ^8$, $SZ^8$, and $NZ^8Z^9$; and
$Z^{12}$ is selected from the group of H, halogen, alkyl, substituted alkyl, aryl, and substituted aryl;
with the proviso that when $R^1$ is

$G^1$, $G^2$, $G^3$ and $G^4$ cannot simultaneously have the following meanings:
$G^1$ and $G^2$=H, $G^3$=O and $G^4$=H or $Z^2C=O$ where $Z^2$=alkyl group
and with the proviso that when $R^1$ is $G^1$, $G^2$, and $G^5$ cannot simultaneously have the following meanings: $G^1$ and $G^2$=H, and $G^5$=F.
2. Compound according to claim 1 having general formula Ia

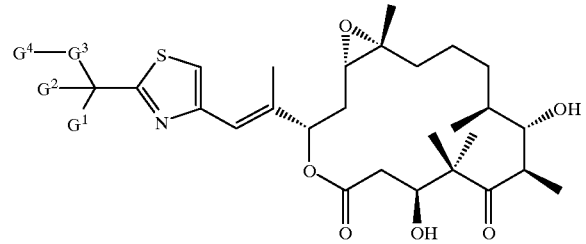

where the symbols have the following meaning:
P—Q is a C,C double bond or an epoxide,
R is a H atom or a methyl group,
$G^1$ is an H atom, an alkyl group, a substituted alkyl group or a halogen atom,
$G^2$ is an H atom, an alkyl group or a substituted alkyl group,
$G^3$ is an O atom, an S atom or an $NZ^1$ group with
$Z^1$ being an H atom, an alkyl group, a substituted alkyl group, an acyl group, or a substituted acyl group, and
$G^4$ is an H atom, an alkyl group, a substituted alkyl group, an $OZ^2$ group, an $NZ^2Z^3$ group, a $Z^2C=O$ group, a $Z^4$ $SO_2$ group or an optionally substituted glycosyl group with
$Z^2$ being a H atom, an alkyl group, a substituted alkyl group, an aryl group, a substituted aryl group or a heterocyclic group,
$Z^3$ an H atom, an alkyl group, a substituted alkyl group, an acyl group or a substituted acyl group, and $Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C$=O with $Z^2$=alkyl group.

3. Compound according to claim 2, wherein $G^3$ is an O atom.

4. Compound according to claim 2, wherein $G^3$ is a S atom.

5. Compound according to claim 2, wherein $G^3$ is $NZ^1$.

6. Compound according to claim 1 having general formula Ib

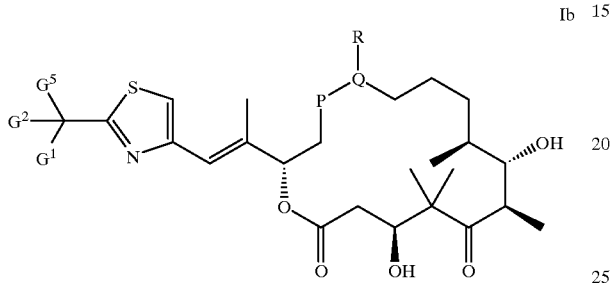

where the symbols have the following meaning:

P—Q is a C,C double bond or an epoxide,

R is a H atom or a methyl group, $G^1$ is a H atom, an alkyl group, a substituted alkyl group or a halogen atom, $G^2$ is a H atom, an alkyl group or a substituted alkyl group, and $G^5$ is a halogen atom, an $N_3$ group, an NCS group, an SH group, a CN group, an NC group or a heterocyclic group.

7. Compound according to claim 6, wherein $G^5$ is an $N_3$ group.

8. Compound according to claim 6, wherein $G^5$ is an NCS group.

9. Compound according to claim 6, wherein $G^5$ is an SH group.

10. Compound according to claim 6, wherein $G^5$ is a CN group.

11. Compound according to claim 6, wherein $G^5$ is an NC group.

12. Compound according to claim 6, wherein $G^5$ is a heterocyclic group.

13. Compound according to claim 1 having general formula IIa

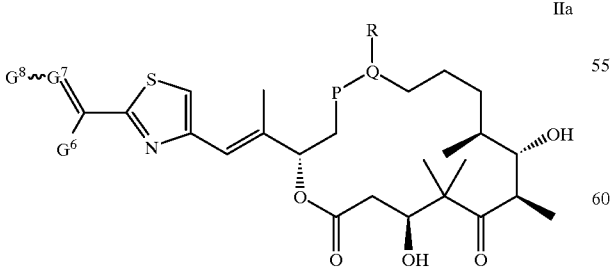

where the symbols have the following meaning:

P—Q is a C,C double bond or an epoxide,

R is a H atom or a methyl group, $G^6$ is a H atom, an alkyl group, a substituted alkyl group or a $CF_3$, $OZ^5$, $SZ^5$ or $NZ^5Z^6$ group with $Z^5$ being a H atom, an alkyl group, a substituted alkyl group, an acyl group or a substituted acyl group, and $Z^6$ being a H atom, an alkyl group or a substituted alkyl group, $G^7$ is a $CZ^7$ group or an N atom with $Z^7$ being a H or halogen atom, an alkyl group, a substituted alkyl group, an aryl group, or a substituted aryl group, or an $OZ^8$, $SZ^8$ or $NZ^8Z^9$ group with $Z^8$ being an H atom or an alkyl group, a substituted alkyl group, an acyl group or a substituted acyl group, and $Z^9$ being a H atom, an alkyl group or a substituted alkyl group, and $G^8$ being a H or a halogen atom, an alkyl group, a substituted alkyl group or an $OZ^{10}$, $SZ^{10}$ or $NZ^{10}Z^{11}$ group with $Z^{10}$ being a H atom, an alkyl group, a substituted alkyl group, an acyl group, a substituted acyl group, an aryl group, or a substituted aryl group, and $Z^{11}$ being a H atom, an alkyl group, a substituted alkyl group, an acyl group, or a substituted acyl group.

14. Compound according to claim 1 having general formula IIb

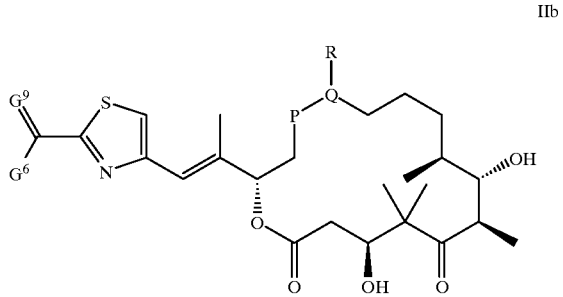

where the symbols have the following meaning:

P—Q is a C,C double bond or an epoxide,

R is a H atom or a methyl group, $G^6$ is a H atom, an alkyl group, a substituted alkyl group or a $CF_3$, $OZ^5$, $SZ^5$ or $NZ^5Z^6$ group with $Z^5$ being a H atom, an alkyl group, a substituted alkyl group, an acyl group or a substituted acyl group, and $Z^6$ being a H atom, an alkyl group or a substituted alkyl group, and $G^9$ is an O or S atom or an —N=N— group.

15. Compound according to claim 14, wherein $G^9$ is an O atom.

16. Compound according to claim 1 having general formula III

III

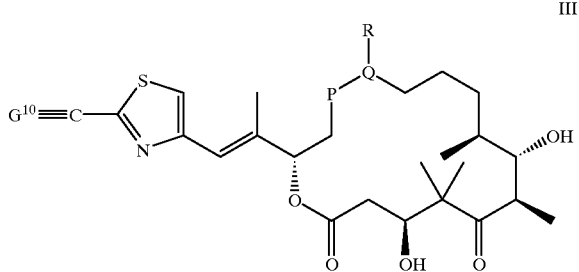

where the symbols have the following meaning:
P—Q is a C,C double bond or an epoxide,
R is a H atom or a methyl group,
$G^{10}$ is an N atom or a $CZ^{12}$ group with
$Z^{12}$ being a H or halogen atom, an alkyl group, a substituted alkyl group, an aryl group, or a substituted aryl group.

17. Compound according to claim 16, wherein $G^{10}$ is an N atom.

18. Compound according to claim 16, wherein $G^{10}$ is a $CZ^{12}$ group.

19. Compound according to claim 1 having general formula IV

IV

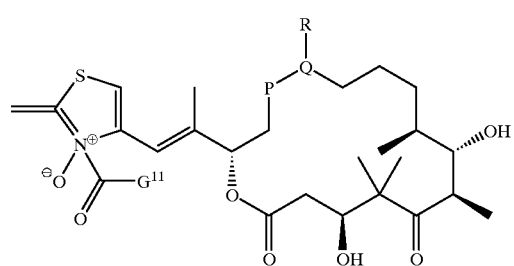

where the symbols have the following meaning:
P—Q is a C,C double bond or an epoxide,
R is a H atom or a methyl group, and
$G^{11}$ is an $R_2N$ group, a substituted $H_2N$ group, an alkyl group, a substituted alkyl group, an aryl group or a substituted aryl group.

20. Compound selected from the group consisting of:
[1S-[1R*,3R*(E),7R*,10S*,11R*,12R*,16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5, 9-dione;
[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5, 9-dione;
[1S-[1R*,3R*(E),7R*,10S*,11R*,12R*,16S*]]-3-[2-[2-[[[(1,1-Dimethylethoxy) carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;
[4S-[4R*,7S*,8R*,9R*,15R*(E)]]-16-[2-[2-[[[(1,1-Dimethylethoxy)carbonyl]amino]methyl]-4-thiazolyl]-1-methyl-ethenyl]-4,8-dihydroxy-5,5,7,9,13-pentamethyl-1-oxa-13(Z)-cyclohexadecene-2,6-dione;
[4S-[4R*,7S*,8R*,9R*,15R*(E)]]-16-[2-[2-(Aminomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-7,11-Dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-3-[2-(3-Acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide;
[1S-[1R*,3R*(E),7R*,10S*,11R*,12R*,16S*]]-7,11-Dihydroxy-3-[2-[2-(methoxymethyl)-4-thiazolyl]-1-methylethenyl]-8,8,10,12-tetramethyl-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12,16-pentamethyl-3-[1-methyl-2-[2-(phenoxymethyl)-4-thiazolyl]ethenyl]-4,17-dioxabicyclo[14.1.0]heptadecane-5,9-dione;
[1S-[1R*,3R*(E),7R*,10S*,11R*,12R*,16S*]]-3-[2-[2-[(Ethylthio)methyl]-4-thiazolyl]-1-methylethenyl]-7,11-dihydroxy-8,8,10,12,16-pentamethyl-4,17-dioxabicyclo[14.1.0]heptadecane-5,9-dione;
[1S-[1R*,3R*(E),7R*,10S*,11R*,12R*,16S*]]-3-[2-[2-(Ethoxymethyl)-4-thiazolyl]-1-methylethenyl]-7,11-dihydroxy-8,8,10,12-tetramethyl-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12-tetramethyl-3-[1-methyl-2-[2-[((2,3,4,6-tetraacetyl-alpha-glucosyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12-tetramethyl-3-[1-methyl-2-[2-[(2',3',4',6'-tetraacetyl-beta-glucosyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12-tetramethyl-3-[1-methyl-2-[2-[(6'-acetyl-alpha-glucosyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-7,11-Dihydroxy-8,8,10,12,16-pentamethyl-3-[1-methyl-2-[2-[(p-toluenesulfonyloxy)methyl]-4-thiazolyl]ethenyl]-4,17-dioxabicyclo[14.1.0]heptadecane-5,9-dione;
[1S-[1R*,3R*(E),7R*,10S*,11R*,12R*,16S*]]-3-[2-[2-(Bromomethyl)-4-thiazolyl]-1-methylethenyl]-7,11-dihydroxy-8,8,10,12-tetramethyl- 4,17-dioxabicyclo[14.1.0]heptadecane-5,9-dione;
[1S-[1R*,3R*(E),7R*,10S*,11R*,12R*,16S*]]-3-[2-(5-Bromo-2-methyl-4-thiazolyl)-1-methylethenyl]-7,11-dihydroxy-8,8,10,12-tetramethyl-4,17-dioxabicyclo[14.1.0]heptadecane-5,9-dione;
[1S-[1R*,3R*(E),7R*,10S*,11R*,12R*,16S*]]-3-[2-[2-(Cyanomethyl)-4-thiazolyl]-1-methylethenyl]-7,11- dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-(Cyanomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-3-[2-[2-(1H-imidazol-1-ylmethyl)-4-thiazolyl]-1-methylethenyl]-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Ethenyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(methoxyimino)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(2-Acetyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Ethynyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[[[2-(Dimethylamino)ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[(Dimethylamino)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[Bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid methyl ester and the pharmaceutically acceptable salts, solvents and hydrates thereof.

21. Method for the preparation of a compound having formula 9, corresponding to general formula Ia, wherein $G^1$ and $G^2$ ar H atoms, $G^3$ is $NZ^1$, and $Z^1$ and $G^4$ are H atoms,

9

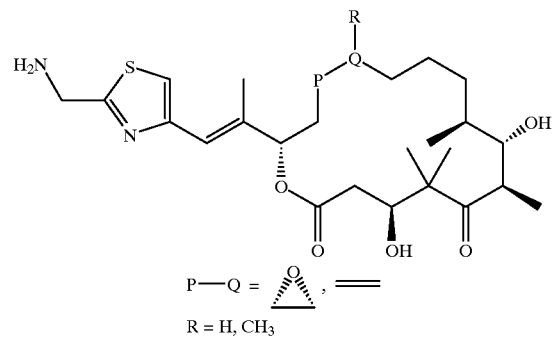

wherein a compound having formula 4 or 5

4

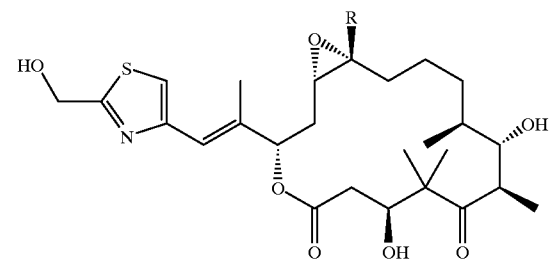

5

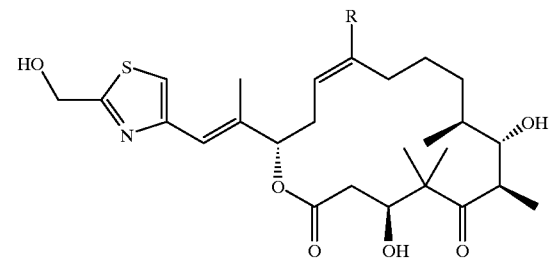

is first activated and subsequently subjected to a nucleophilic displacement to obtain a compound having formula 7

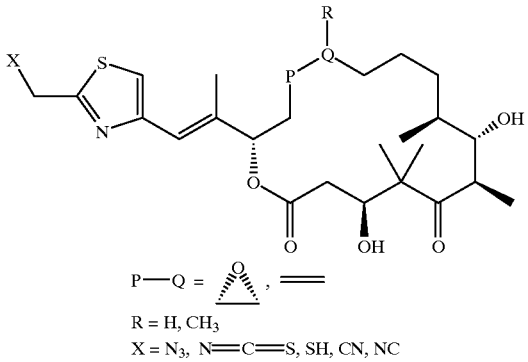

R = H, CH₃
X = N₃, N=C=S, SH, CN, NC wherein the resulting compound having formula 7 is reduced to form a compound having formula 9, where
P—Q=CH=C or CH . . . C, where . . . is a C—C single bond with an epoxide O bridge,
R=a hydrogen atom or a methyl group and
X=N₃.

22. Method according to claim 21, wherein (i) the activation is carried out with TosHal (Hal=Cl, Br or I) and pyridine and the nucleophilic displacement with NaN₃ or (ii) that activation and nucleophilic displacement are carried out with diazabicycloundecene (DBU) and diphenylphosphoryl azide (DPPA).

23. Method according to claim 21, wherein the reduction is carried out (i) as a hydrogenation with the aid of a Lindlar catalyst or (ii) with a phosphine.

24. A pharmaceutical composition which comprises as active ingredient an amount of at least one compound selected from the group consisting of a compound of the general formula according to claim 1 and a pharmaceutically acceptable salt thereof, and one or more pharmaceutically acceptable carriers, excipients or diluents thereof.

25. A pharmaceutical composition of claim 24 which comprises as active ingredient an amount of at least one compound which is an anti-cancer or cytotoxic agent.

26. A pharmaceutical composition of claim 25 wherein the anti-cancer or cytotoxic agent is selected from the group consisting of

[1S-[1R*,3R*(E),7R*,10S*,11R*,12R*,16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[[(1,1-Dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-[[[(1,1-Dimethylethoxy)carbonyl]amino]methyl]-4-thiazolyl]-1-methyl-ethenyl]-4,8-dihydroxy-5,5,7,9,13-pentamethyl-1-oxa-13(Z)-cyclohexadecene-2,6-dione;

[4S-[4R*,7S*,8R*,9R*,15R*(E)]]-16-[2-2-(Aminomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(3-Acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione, N-oxide;

[1S-[1R*,3R*(E),7R*,10S*,11R*,12R*,16S*]]-7,11-Dihydroxy-3-[2-[2-(methoxymethyl)-4-thiazolyl]-1-methylethenyl3-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-(phenoxymethyl)-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[(Ethylthio)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(Ethoxymethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(2,3,4,6-tetraacetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(2',3',4',6'-tetraacetyl-beta-glucosyloxy)methyl]-4-thiazolyl]ethenyl]- 4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[(6'-acetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(p-toluenesulfonyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-(Bromomethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(5-Bromo-2-methyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-[2-(Cyanomethyl)-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-(Cyanomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-Dihydroxy-3-[2-[2-(1H-imidazol-1-ylmethyl)-4-thiazolyl]-1-methylethenyl]-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Formyl-4-thiazolyl)-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-Ethenyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(methoxyimino)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(2-Acetyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-Ethynyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[[[2-(Dimethylamino)ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[(Dimethylamino)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[Bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid;

[1S-[1R*,3R*(E),7R*,10S*,11R*,12R*,16S*]]-4-[2-(7,11-Dihydroxy-8,8,10,12-tetramethyl-5,9-dioxo-4,17-dioxabicyclo[14.1.0]heptadecan-3-yl)-1-propenyl]-2-thiazolecarboxylic acid methyl ester and the pharmaceutically acceptable salts, solvents and hydrates thereof.

27. Method of treating cancer or other proliferative disease in a patient in need of said treatment which comprises administering a therapeutically effective amount of the pharmaceutical composition according to claim 24.

28. Method of providing an antiangiogenic effect in a patient in need of said treatment which comprises administering a therapeutically effective amount of the pharmaceutical composition according to claim 24.

29. Method of treating cancer or other proliferative disease in a patient in need of said treatment which comprises administering a therapeutically effective amount of the pharmaceutical composition according to claim 24, and which further comprises administering either simultaneously or sequentially another therapeutic agent useful for said treatment.

\* \* \* \* \*